United States Patent [19]
Chin et al.

[11] Patent Number: 5,468,248
[45] Date of Patent: Nov. 21, 1995

[54] ENDOSCOPIC INFLATABLE RETRACTION DEVICES FOR SEPARATING LAYERS OF TISSUE

[75] Inventors: Albert K. Chin, Palo Alto; John P. Lunsford, San Carlos, both of Calif.

[73] Assignee: Origin Medsystems, Inc., Menlo Park, Calif.

[21] Appl. No.: 111,211

[22] Filed: Aug. 24, 1993

Related U.S. Application Data

[60] Division of Ser. No. 911,714, Jul. 10, 1992, which is a continuation-in-part of Ser. No. 794,590, Nov. 19, 1991, Pat. No. 5,309,896, which is a continuation-in-part of Ser. No. 706,781, May 29, 1991, abandoned.

[51] Int. Cl.$^6$ ..................................................... A61B 17/02
[52] U.S. Cl. ............................................. 606/192; 600/207
[58] Field of Search .................................. 128/20; 606/1, 606/151, 185, 190–194, 213; 604/96–101, 164, 167, 169, 170

[56] References Cited

U.S. PATENT DOCUMENTS

| | | | |
|---|---|---|---|
| 3,774,596 | 11/1973 | Cook | 128/5 |
| 3,782,370 | 1/1974 | McDonald | 128/20 |
| 3,831,587 | 8/1974 | Boyd et al. | 128/6 |
| 3,863,639 | 2/1975 | Kleaveland . | |
| 4,083,369 | 4/1978 | Sinnreich . | |
| 4,240,433 | 7/1981 | Bordow . | |
| 4,291,687 | 9/1981 | Sinnreich . | |
| 4,430,076 | 2/1984 | Harris | 604/96 |
| 4,447,227 | 5/1984 | Kotsanis | 604/95 |
| 4,598,699 | 7/1986 | Garren et al. | 128/4 |
| 4,775,371 | 10/1988 | Mueller, Jr. | 604/280 |
| 4,779,611 | 10/1988 | Grooters et al. | 128/4 |

(List continued on next page.)

FOREIGN PATENT DOCUMENTS

| | | |
|---|---|---|
| 516114 | 5/1981 | Australia . |
| 0010650 | 5/1980 | European Pat. Off. . |
| 0246086 | 11/1987 | European Pat. Off. . |
| 0251976 | 1/1988 | European Pat. Off. . |
| 0275230 | 7/1988 | European Pat. Off. . |
| 0480653 | 4/1992 | European Pat. Off. ............... 604/164 |
| WO93/11824 | 12/1992 | European Pat. Off. . |
| 2474304 | 7/1981 | France . |
| 2646088 | 10/1990 | France . |
| 2688695 | 5/1992 | France . |
| 2847633 | 5/1979 | Germany . |
| 9104383 | 7/1991 | Germany . |
| 797668 | 1/1991 | U.S.S.R. ................................. 128/20 |
| 2071502 | 9/1981 | United Kingdom . |

OTHER PUBLICATIONS

M. M. Gazayerli, "the Gazayerli Endoscopic Retractor, Model 1;" Surgical Laparoscopy & Endoscopy, vol. 1, No. 2, pp. 98–100 Raven Press, New York, Jun. 1991.

*Primary Examiner*—Stephen C. Pellegrino
*Assistant Examiner*—Glenn Dawson
*Attorney, Agent, or Firm*—Limbach & Limbach; Ian Hardcastle

[57] ABSTRACT

A system for separating a first layer of tissue from a second layer of tissue and for maintaining separation of the first layer of tissue from the second layer of tissue while providing access to at least one of the layers of tissue. The system comprises a main envelope which defines a main inflatable chamber, an introducing means and an insufflating means. The introducing means includes a main cannula portion to which the main envelope is attached. The introducing means is for introducing the main envelope in a collapsed state between the first layer of tissue and the second layer of tissue, and for inflating the main envelope into an expanded state to separate the first layer of tissue from the second layer of tissue, and to create a working space between the first layer of tissue and the second layer of tissue. The insufflating means includes an auxiliary cannula portion to which an auxiliary envelope defining an auxiliary inflatable chamber is attached. The insufflating means is for introducing insufflation gas into the working space to maintain the separation of the first layer of tissue from the second layer of tissue.

34 Claims, 20 Drawing Sheets

U.S. PATENT DOCUMENTS

| | | | |
|---|---|---|---|
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,082,005 | 1/1992 | Kaldany . | |
| 5,122,122 | 6/1992 | Allgood . | |
| 5,122,155 | 6/1992 | Eberbach | 606/213 |
| 5,141,515 | 8/1992 | Eberbach | 128/887 |
| 5,147,316 | 9/1992 | Castillenti | 604/164 |
| 5,176,692 | 1/1993 | Wilk et al. | 606/151 |
| 5,176,697 | 1/1993 | Hasson et al. | 606/191 |
| 5,188,630 | 2/1993 | Christaudias | 606/191 |
| 5,195,507 | 3/1993 | Bilweis | 604/97 |
| 5,201,742 | 4/1993 | Hasson | 606/1 |
| 5,250,025 | 10/1993 | Sosnowski et al. | 604/101 |
| 5,269,753 | 12/1993 | Wilk | 604/49 |
| 5,359,995 | 11/1994 | Sewell | 606/192 |

PERITONEUM P
SUBPERITONEAL FAT FL
FASCIA TRANSVERSALIS F
TRANSVERSUS
INTERNAL OBLIQUE
EXTERNAL OBLIQUE
APONEUROSIS
SUBCUTANEOUS FAT
SKIN S

SCROTUM

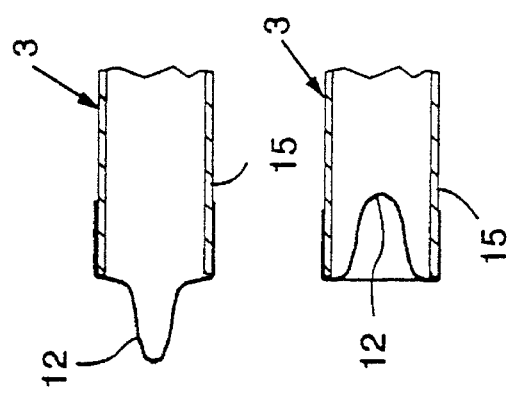
FIG. 2B
FIG. 2C
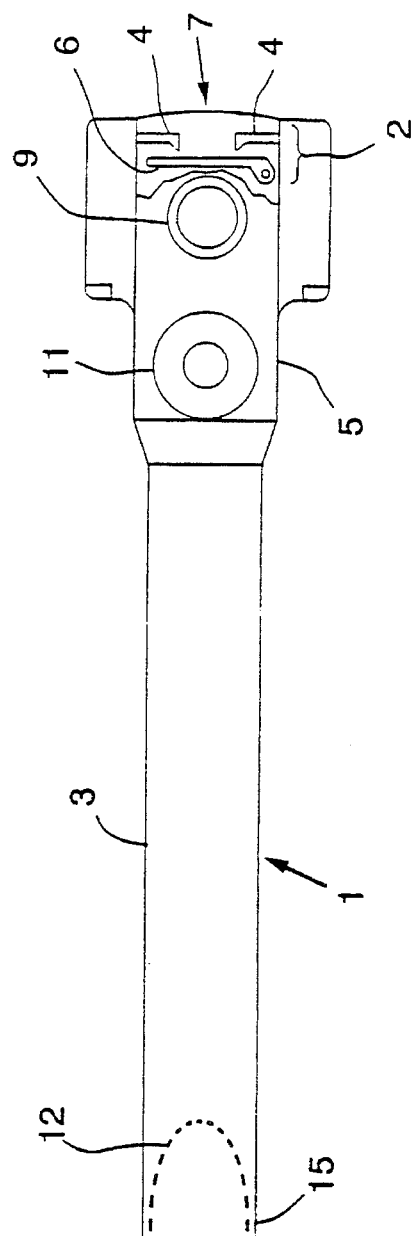
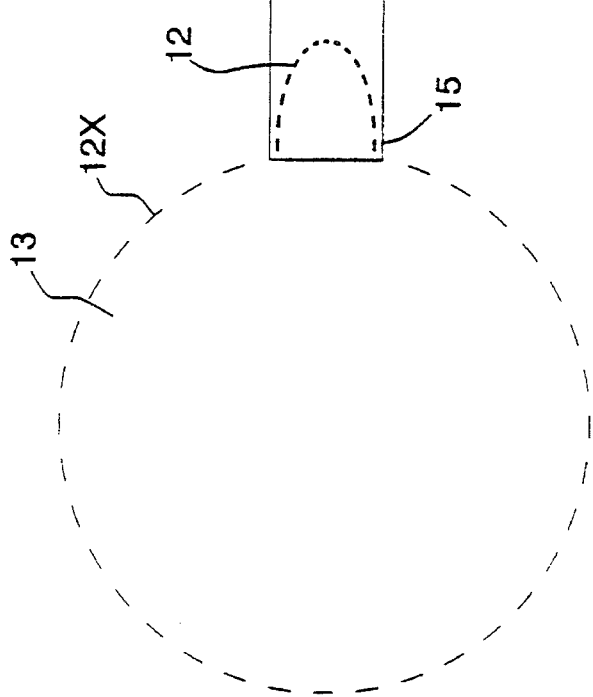
FIG. 2A

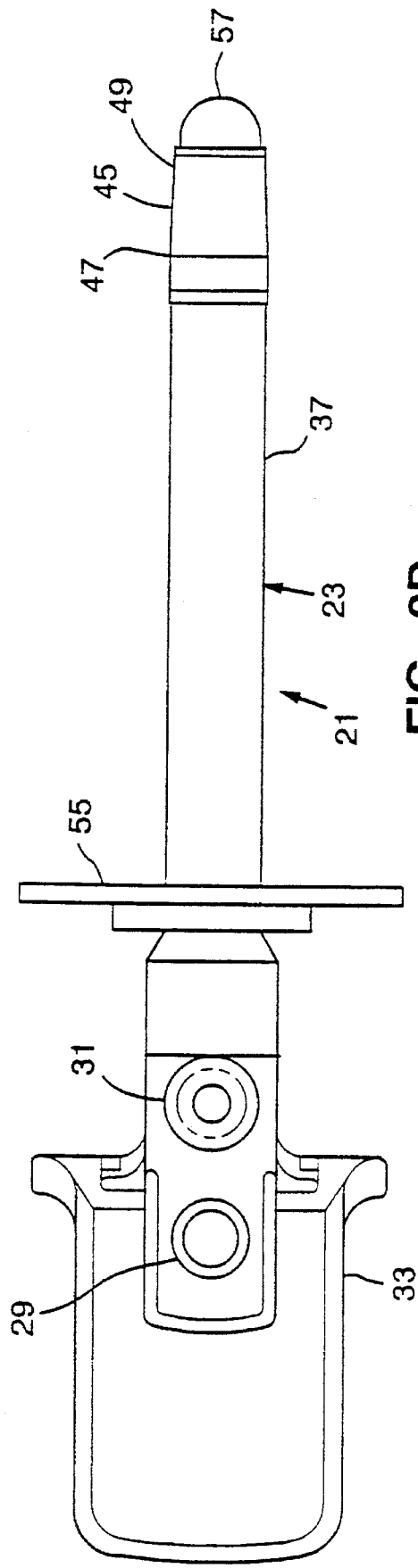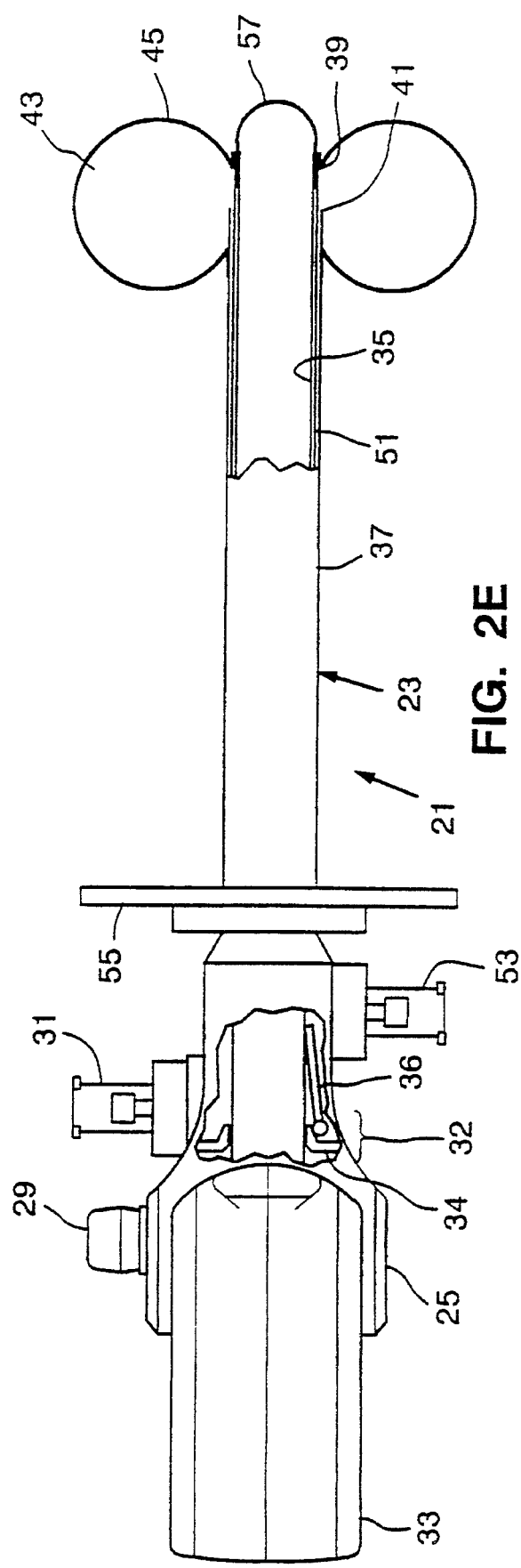

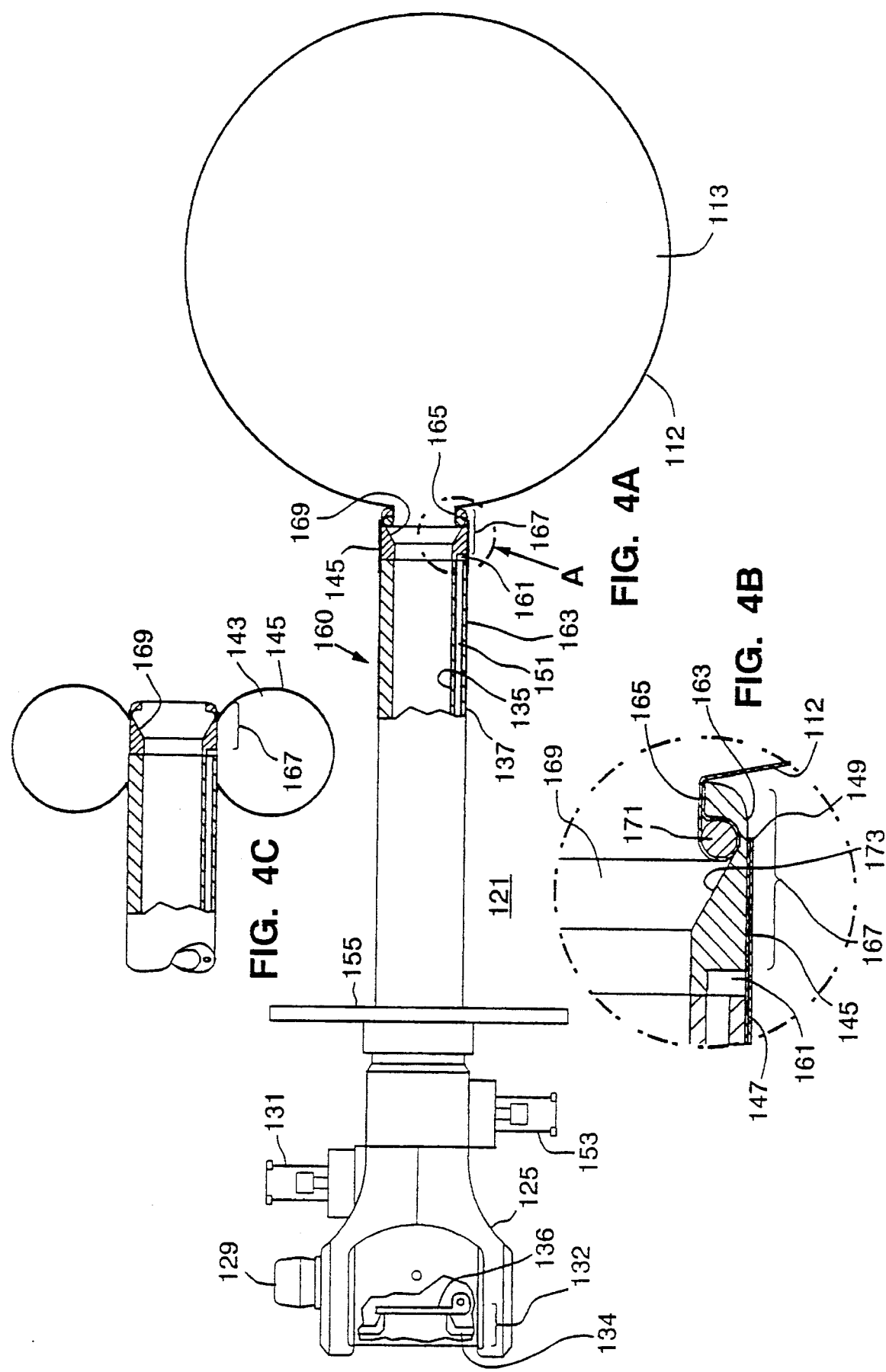

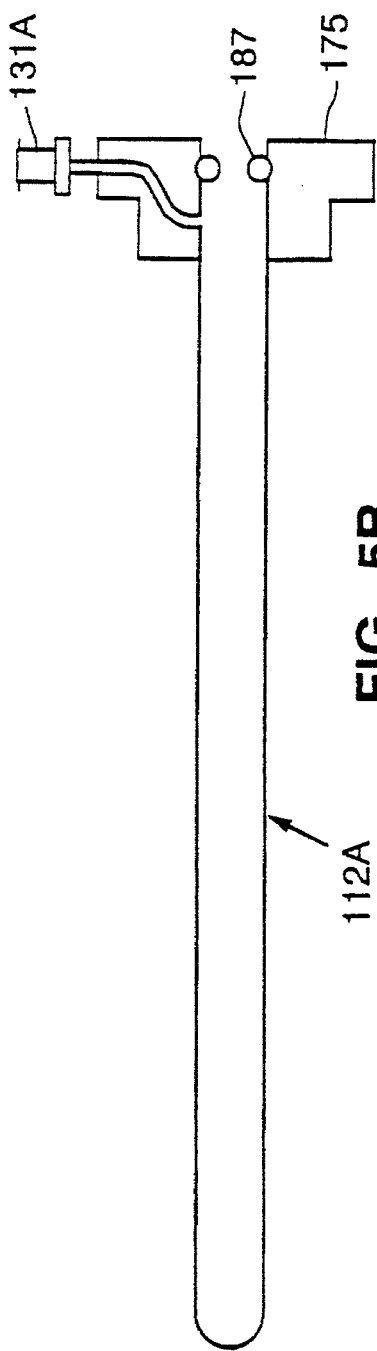
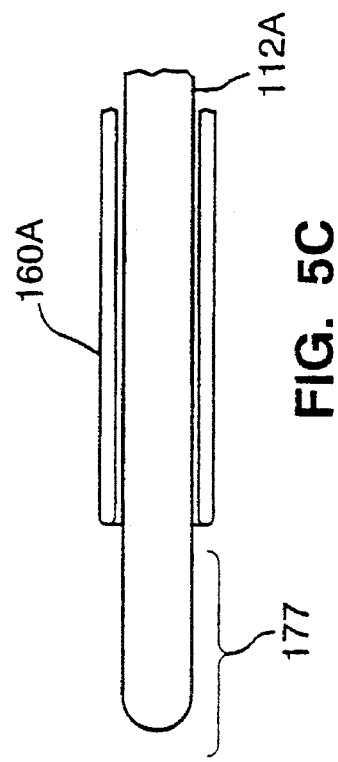
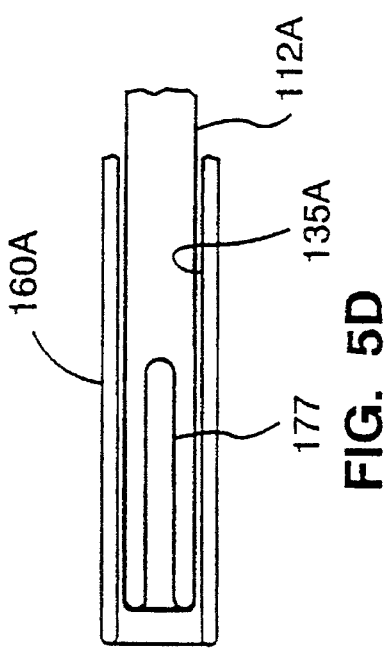
FIG. 5B
FIG. 5C
FIG. 5D

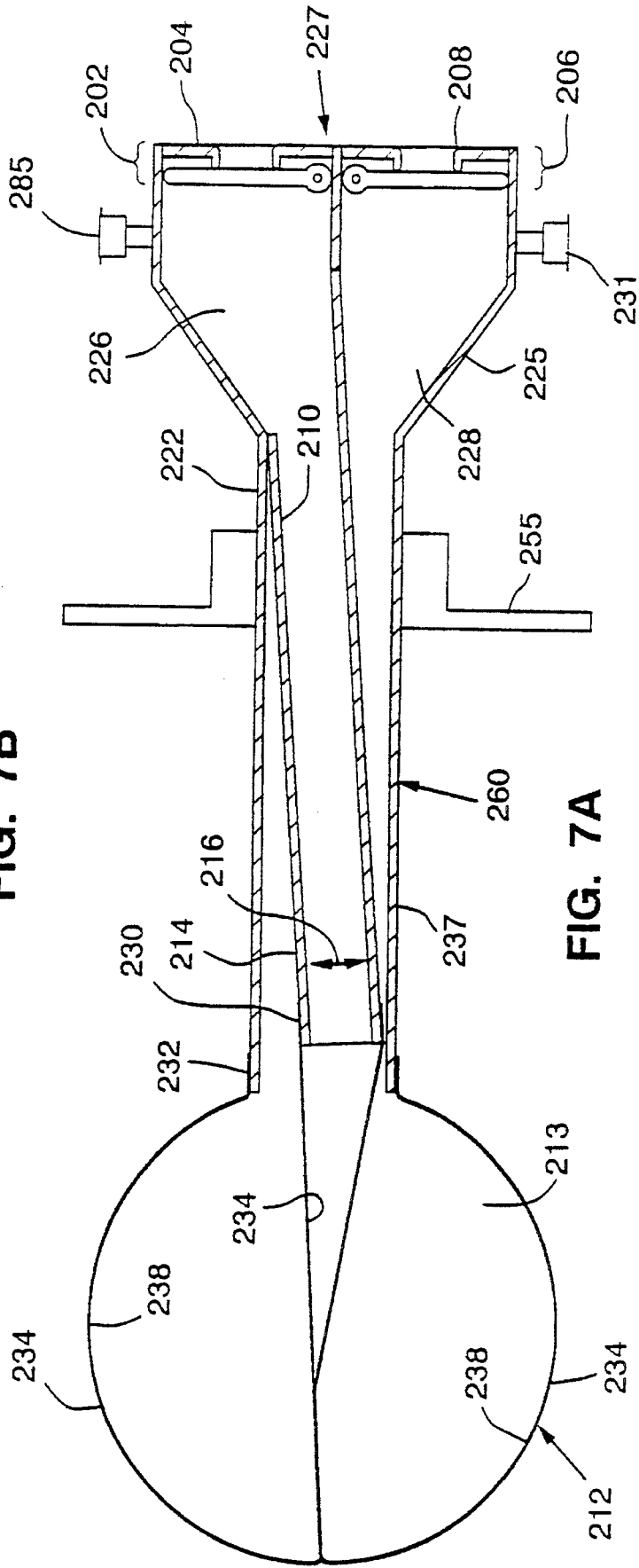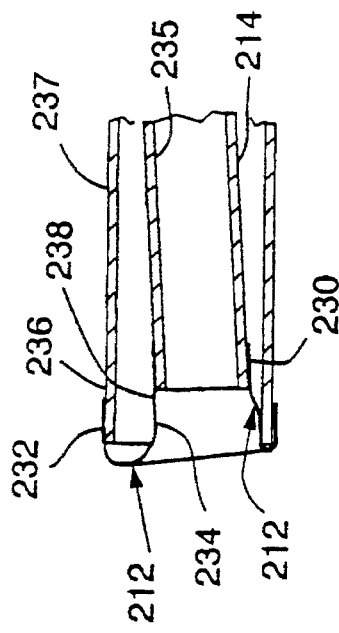
FIG. 7B
FIG. 7A

ENDOSCOPIC INFLATABLE RETRACTION DEVICES FOR SEPARATING LAYERS OF TISSUE

This application is a divisional of pending application Ser. No. 07/911,714, filed Jul. 10, 1992, of inventors Albert K. Chin and John P. Lunsford, which is a continuation-in-Part of application Ser. No. 794,590, filed Nov. 19, 1991, of inventors Frederic H. Moll, Charles Gresl, Jr., Albert K. Chin, and Philip K. Hopper, now U.S. Pat. No. 5,309,896, which is a Continuation-in-Part of application Ser. No. 706,781, filed May 29, 1991, of inventors Frederic H. Moll, Albert K. Chin, Diane E. Caramore, and Frank T. Watkins III now abandoned.

BACKGROUND OF THE INVENTION

A hernia is the protrusion of part of a body pan or structure through a defect in the wall of a surrounding structure. Most commonly, a hernia is the protrusion of part of abdominal contents, including bowel, through a tear or weakness in the abdominal wall, or through the inguinal canal into the scrotum.

An abdominal hernia is repaired by suturing or stapling a mesh patch over the site of the tear or weakness. The mesh patch has a rough surface that can irritate the bowel and cause adhesions. It is therefore preferred to install the patch properitoneally. The mesh patch is preferably attached to the properitoneal fascia of the abdominal wall, and covered by the peritoneum. To attach the mesh patch to the properitoneal fascia, the peritoneum must be dissected from the properitoneal fascia. This is a difficult process. There is a risk of puncturing the peritoneum. Moreover, strands of properitoneal fat interconnecting the peritoneum and the properitoneal fascia make it difficult to see the site of the hernia.

The use of laparoscopic techniques to perform hernia repair is becoming increasingly common. In the conventional procedure for carrying out a hernia repair laparoscopically, an endoscope and instruments are introduced into the belly through one or more incisions in the abdominal wall, and are advanced through the belly to the site of the hernia. Then, working from inside the belly, a long incision is made in the peritoneum covering the site of the hernia. Part of the peritoneum is dissected from the properitoneal fat layer to provide access to the fat layer. This is conventionally done by blunt dissection, such as by sweeping a rigid probe under the peritoneum. In this procedure, it is difficult to dissect the peritoneum cleanly since patchy layers of properitoneal fat tend to adhere to the peritoneum.

In an alternative known laparoscopic hernia repair procedure, the belly is insufflated. An incision is made in the abdominal wall close to the site of the hernia. The incision is made through the abdominal wall as far as the properitoneal fat layer. The peritoneum is then blunt dissected from the properitoneal fat layer by passing a finger or a rigid probe through the incision and sweeping the finger or rigid probe under the peritoneum. After the peritoneum is dissected from the properitoneal fat layer, the space between the peritoneum and the properitoneal fat layer is insufflated to provide a working space in which to apply the mesh patch to the properitoneal fascia. During the blunt dissection process, it is easy to puncture through the peritoneum, which is quite thin. A puncture destroys the ability of the space between the peritoneum and the fascia to hold gas insufflation. Also, it is difficult to dissect the peritoneum cleanly since patchy layers of properitoneal fat tend to adhere to the peritoneum.

U.S. patent application Ser. No. 794,590, of which application this application is a Continuation-in-Part, discloses a laparoscopic hernia repair technique that enables a mesh patch to be attached to the properitoneal fascia without breaching the peritoneum. An incision is made through the abdominal wall as far as the properitoneal fat layer. A multi-chambered inflatable retraction device is pushed through the incision into contact with the peritoneum, and is used to separate the peritoneum from the underlying layers. The main end chamber of the inflatable retraction device is then inflated to elongate the inflatable retraction device towards the site of the hernia. As it inflates, the inflatable retraction device gently separates the peritoneum from the underlying layers. Once the main chamber of the inflatable retraction device is fully inflated, a second inflatable chamber is inflated. The second inflatable chamber enables the inflatable retraction device continue to separate the peritoneum from the underlying layers after the main inflatable chamber has been deflated.

One or more apertures are then cut in the envelope of the main inflatable chamber to provide access to the site of the hernia for instruments passed into the main chamber. With such an arrangement, instruments pass through the main chamber situated between the peritoneum and the underlying layers. In this way, a gauze patch can be attached to the properitoneal fascia without breaching the peritoneum.

SUMMARY OF THE INVENTION

The invention provides an apparatus for separating a first layer of tissue, such as the peritoneum, from a second layer of tissue, such as the properitoneal fascia. The apparatus includes a main envelope that defines a main inflatable chamber. The apparatus also includes an introducing device for introducing the main envelope in a collapsed state between the first layer of tissue and the second layer of tissue. The introducing device is also for inflating the main envelope into an expanded state to separate the first layer of tissue from the second layer of tissue, and to create a working space between the first layer of tissue and the second layer of tissue. Finally, the apparatus includes an insufflating device for introducing insufflation gas into the working space between the first layer of tissue and the second layer of tissue.

In a method according to the invention of separating a first layer of tissue from a second layer of tissue, a main envelope and insufflation gas are provided. The main envelope defines a main inflatable chamber. The main envelope is introduced in a collapsed state between the first layer of tissue and the second layer of tissue. The main envelope is inflated into an expanded state to separate the first layer of tissue from the second layer of tissue, and to create a working space between the first layer of tissue and the second layer of tissue. Finally, insufflation gas is introduced into the working space between the first layer of tissue and the second layer of tissue.

In a first practical embodiment of an apparatus according to the invention, the main envelope and the introducing device constitute a first component that separates the first layer of tissue from the second layer of tissue to create the working space. The insufflation device constitutes a second component, which insufflates the working space to maintain the separation of the first layer of tissue from the second. The insufflation device is tubular, has an anchor flange slidably mounted on it, and has a toroidal inflatable chamber at its distal end. The anchor flange and toroidal inflatable chamber together form a gas-tight seal with the second layer of tissue.

In a method according to the invention of using the two-component apparatus, the introducing device is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create a working space between the two layers of tissue. An endoscope may be passed through the bore of the introducing device into the main chamber to observe the extent of separation of the layers of tissue. The main envelope is then returned to a collapsed state, and the main envelope and the introducing device are removed from the incision.

The insufflating device is inserted into the incision so that its distal end projects into the working space between the two layers of tissue. The toroidal inflatable chamber is Mated into an expanded state. The anchor flange is slid distally along the insufflating device to compress the second layer of tissue between it and the expanded toroidal inflatable chamber, and thus to form a gas-tight seal. Insufflating gas is then passed through the insufflating device into the working space to maintain the separation of the first layer of tissue from the second. An endoscope may be passed through the bore of the insufflating device into the working space to observe within the working space.

In a first embodiment of a one-component apparatus according to the invention, the introducing device is also for returning the main envelope to a collapsed state. A single elongated tube provides the introducing device and the insufflating device. The main envelope is detachable from the single elongated tube. The single elongated tube has an anchor flange slidably mounted on it, and has a toroidal inflatable chamber at its distal end. The anchor flange and toroidal inflatable chamber together form a gas-tight seal with the second layer of tissue.

In a method according to the invention of using the first embodiment of a one-component apparatus according to the invention to separate a first layer of tissue from a second layer of tissue, the elongated tube is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create a working space between the two layers of tissue. An endoscope may be passed through the bore of the single elongated tube into the main chamber to observe the extent of separation of the layers of tissue. The main envelope is then returned to a collapsed state, detached from the elongated tube, and removed from the working space between the layers of tissue through the bore of the elongated tube.

The toroidal inflatable chamber at the distal end of the elongated tube is inflated into an expanded state. The anchor flange is slid distally along the elongated tube to compress the second layer of tissue between it and the expanded toroidal inflatable chamber, to form a gas-tight seal. Insufflating gas is then passed through the elongated tube into the working space to maintain the separation of the first layer of tissue from the second. An endoscope may be passed through the bore of the single elongated tube into the working space to observe within the working space.

In a second embodiment of a one-component apparatus according to the invention, the introducing device is an outer elongated tube, and the insufflating device is an inner elongated tube mounted in the bore of the outer elongated tube. The proximal ends of the tubes are flexibly coupled together. The main envelope is a cylindrical piece of elastomeric material. One end of the main envelope is everted with respect to the other, and is attached to the distal end of the outer elongated tube. The other end of the main envelope is attached to the distal end of the inner elongated tube. The main inflatable chamber defined by the main envelope is thus substantially toroidal. The outer elongated tube has an anchor flange slidably mounted on it. The anchor flange and the main inflatable chamber together form a gas-tight seal with the second layer of tissue.

In a method according to the invention of using the second embodiment of a one-component apparatus according to the invention to separate a first layer of tissue from a second layer of tissue, the outer elongated tube is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create working a space between the layers of tissue. An endoscope may be passed through the outer elongated tube into the main chamber to observe the extent of separation of the layers of tissue.

The anchor flange is slid distally along the introducing device tube to compress the second layer of tissue between it and the main inflatable chamber, to form a gas-tight seal. Insufflating gas is then passed through the bore of the inner elongated tube and the bore of the main envelope into the working space to maintain the separation of the first layer of tissue from the second. An endoscope may be passed through the bore of the inner elongated tube and the bore of the main envelope into the working space to observe within the working space.

In a further method according to the invention, access through the abdominal wall to repair a hernia is provided. The abdominal wall includes the peritoneum and an underlying layer. A main envelope and an insufflation gas are provided. The main envelope defines a main inflatable chamber. The main envelope is introduced in a collapsed state between the peritoneum and the underlying layer. The main envelope is inflated into an expanded state to separate the peritoneum from the underlying layer, and to create a working space between the peritoneum and the underlying layer. Insufflation gas is introduced into the working space, and the hernia is repaired using an instrument passed into the working space.

In a final method according to the invention, access is provided through the abdominal wall from near the umbilicus to repair a hernia. The abdominal wall includes the peritoneum and an underlying layer. A main envelope and insufflation gas are provided. The main envelope defines a main inflatable chamber. An incision is made at the umbilicus through the abdominal wall, including the underlying layer, excluding the peritoneum. The main envelope is introduced in a collapsed state into the incision to bring the main envelope into contact with the peritoneum. The main envelope is inflated into an expanded state to separate a portion of the peritoneum from the underlying layer, and to create a space between the portion of the peritoneum and the underlying layer. The main envelope is returned to a collapsed state. The main envelope is advanced in the direction of the hernia to the boundary of the separated portion of the peritoneum. The main envelope is re-inflated into an expanded state to separate an additional portion of the peritoneum from the underlying layer, and to enlarge the space. Finally, insufflation gas is introduced into at least part of the space.

In a variation, the collapsing, advancing, and re-inflating steps are repeated with the main envelope being expanded to a partially expanded state to create a narrow tunnel between the incision at the umbilicus and the hernia. At the hernia, the main inflatable chamber is inflated into a fully expanded state to create a working space that is later insufflated.

BRIEF DESCRIPTION OF THE DRAWINGS

FIGS. 2A through 2E show a two-component apparatus according to the invention, wherein:

FIG. 2A shows the separation component of the two-component apparatus according to the invention.

FIG. 2B shows pan of the distal pan of the separation component of the two-component apparatus according to the invention with the main envelope in its evened position.

FIG. 2C shows pan of the distal pan of the separation component of the two-component apparatus according to the invention with the main envelope in its inverted position.

FIG. 2D shows the insufflation component of the two-component apparatus according to the invention with the toroidal inflatable chamber in its collapsed state.

FIG. 2E shows the insufflation component of the two-component apparatus according to the invention with the toroidal inflatable chamber in its expanded state.

FIGS. 3A through 3I are longitudinal cross sections of the abdomen illustrating the method according to the invention of using a two-component apparatus according to the invention to separate the peritoneum from the underlying layer, wherein:

FIG. 3A shows an incision made through the abdominal wall, including the properitoneal fat layer, excluding the peritoneum.

FIG. 3B shows the distal pan of the separation component of a two-component apparatus according to the invention inserted into the incision. The separation component includes the main envelope in its collapsed state.

FIG. 3C shows the main envelope inflated to its expanded state to separate the peritoneum from the underlying layer.

FIG. 3D shows the main envelope returned to its collapsed state.

FIG. 3E shows the separation component removed from the incision.

FIG. 3F shows the distal pan of the insufflation component of the two-component apparatus according to the invention inserted into the incision.

FIG. 3G shows the toroidal inflatable chamber of the insufflation component inflated to its expanded state and the anchor flange slid into contact with the skin of the abdominal wall to provide a gas-tight seal.

FIG. 3H shows the working space between the peritoneum and the underlying layer insufflated with a gas passed through the bore of the insufflation component.

FIG. 3I shows additional instruments passed through gas-tight trocar sheaths into the insufflated working space to repair the hernia by attaching a mesh patch to the properitoneal fascia.

FIGS. 4A through 4C show the main embodiment of the first one-component apparatus according to the invention, wherein:

FIG. 4A shows the main embodiment of the first one-component apparatus according to the invention with the main envelope in its expanded state.

FIG. 4B shows details of the area marked "A" at the distal end of the tube assembly in FIG. 4A.

FIG. 4C shows the distal pan of the tube assembly with the toroidal inflatable chamber in its expanded state.

FIGS. 5A through 5D show the alternative embodiment of the first one-component apparatus according to the invent/on, wherein:

FIG. 5A shows the alternative embodiment of the first one-component apparatus according to the invention with the main envelope in its expanded state.

FIG. 5B shows the elongated main envelope of the alternative embodiment of the first one-component apparatus according to the invention.

FIG. 5C shows the distal pan of the tube assembly of the alternative embodiment of the first one-component apparatus according to the invention with the main envelope in its evened state.

FIG. 5D shows the distal part of the tube assembly of the alternative embodiment of the first one-component apparatus according to the invention with the main envelope in its inverted state.

FIGS. 6A through 6H are longitudinal cross sections of the abdomen illustrating the method according to the invention of using a first-one-component apparatus according to the invention to separate the peritoneum from the underlying layer, wherein:

FIG. 6A shows an incision made through the abdominal wall, including the underlying layer, excluding the peritoneum.

FIG. 6B shows the distal pan of the tube assembly of a one-component apparatus according to the invention inserted into the incision. The tube assembly includes the main envelope in its collapsed state.

FIG. 6C shows the main envelope inflated to its expanded state to separate the peritoneum from the underlying layer.

FIG. 6D shows the main envelope returned to its fully collapsed state.

FIG. 6E shows the apparatus advanced into the incision such that the envelope of the toroidal inflatable chamber clears the incision.

FIG. 6F shows the toroidal inflatable chamber inflated to its expanded state.

FIG. 6G shows the anchor flange slid into contact with the skin of the abdominal wall. The anchor flange together with the expanded toroidal inflatable chamber provides a gas-tight seal.

FIG. 6H shows the space between the peritoneum and the underlying layer insufflated with a gas passed through the bore of the apparatus.

FIGS. 7A and 7B show a second embodiment of a one-component apparatus according to the invention, wherein:

FIG. 7A shows the second one-component apparatus according to the invention with the main envelope in its expanded state.

FIG. 7B shows the second one-component apparatus according to the invention with the main envelope in its collapsed state.

FIGS. 9A through 9F are longitudinal cross sections of the abdomen illustrating the method according to the invention of using a second one-component apparatus according to the invention to separate the peritoneum from the underlying layer, wherein:

FIG. 9A shows an incision made through the abdominal wall, including the underlying layer, excluding the peritoneum.

FIG. 9B shows the distal part of the tube assembly of a one-component apparatus according to the invention inserted into the incision. The tube assembly includes the main envelope in its collapsed state.

FIG. 9C shows the main envelope inflated to its expanded state to separate the peritoneum from the underlying layer.

FIG. 9D shows the main envelope returned to its partially-collapsed state.

FIG. 9E shows the anchor flange slid into contact with the skin of the abdominal wall. The anchor flange and the partially-collapsed main inflatable chamber together provide a gas-tight seal.

FIG. 9F shows the space between the peritoneum and the underlying layer insufflated with a gas passed through the bore of the inner tube of the apparatus.

FIGS. 10A through 10H are longitudinal cross sections of the abdomen, wherein:

FIG. 10A shows an incision made through the abdominal wall, including the underlying layer, excluding the peritoneum.

FIG. 10B shows the distal pan of the apparatus according to the invention inserted into the incision. The tube assembly includes the main envelope in its collapsed state.

FIG. 10C shows the main envelope inflated to a partially-expanded state to separate part of the peritoneum from the underlying layer.

FIG. 10D shows the main envelope returned to its collapsed state.

FIG. 10E shows the apparatus advanced in the direction of the groin to bring the main envelope to the limit of the separated pan of the peritoneum.

FIG. 10F shows the main envelope re-inflated to a partially-expanded state to separate an additional part of the peritoneum from the underlying layer.

FIG. 10G shows the main envelope advanced to close to the site of the hernia and re-inflated to its fully inflated state to create a working space.

FIG. 10H shows the introducer component advanced through the tunnel into the working space, and the toroidal inflatable chamber inflated to form a gas-tight seal with the entrance of the tunnel.

FIG. 10I is a plan view of the abdomen showing the insufflator component in position with its distal end in the working space and its toroidal inflatable chamber forming a gas-tight seal with the entrance of the tunnel. The figure also shows the lesser extent to which the peritoneum is detached in the tunnel compared with in the working space.

DETAILED DESCRIPTION OF THE INVENTION

Figure 1:
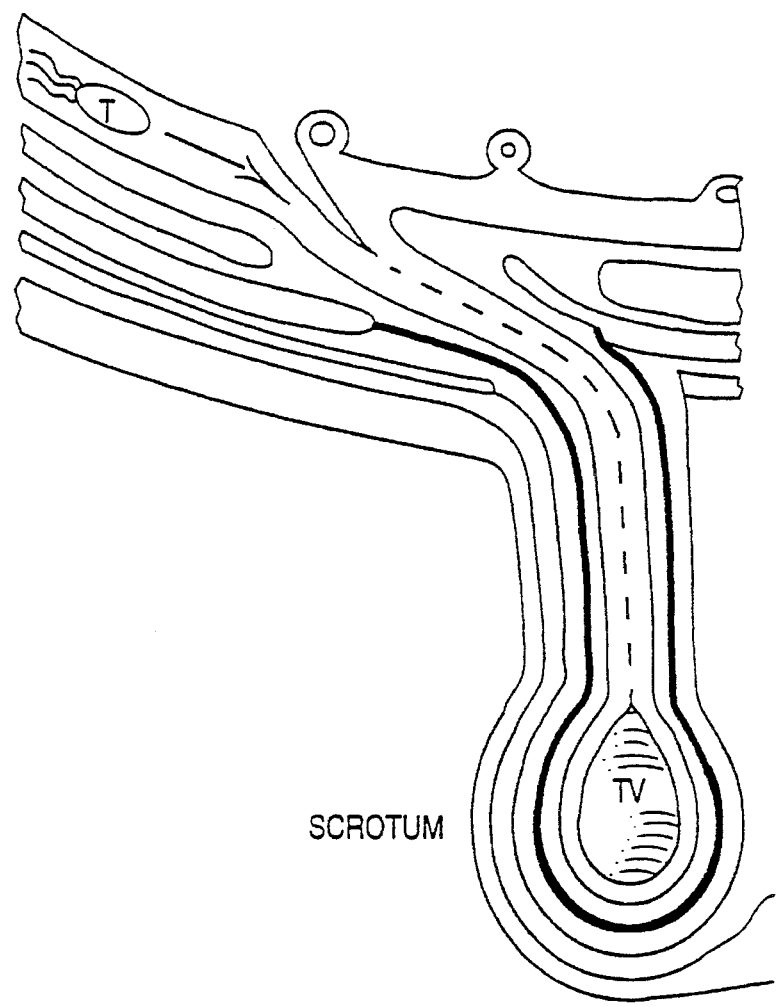
FIG. 1 is a cross-sectional view of the abdominal wall showing the peritoneum, the properitoneal fat layer, the properitoneal fascia, and other tissue layers.

A cross-sectional view of the abdominal wall is shown in FIG. 1. The abdominal wall includes the several layers of tissue shown. The peritoneum P is the innermost layer. Underlying the peritoneum are several layers of tissue, including the properitoneal fat layer FL and the properitoneal fascia F. The properitoneal fascia is the layer to which the mesh patch is preferably attached in hernia repair. The properitoneal fat layer separates the peritoneum from the properitoneal fascia. The properitoneal fat layer is relatively weak, which enables the peritoneum to be separated relatively easily from the fascia. When the peritoneum is separated from the fascia, separation takes place at or in the properitoneal fat layer. The properitoneal fat layer can remain attached to the properitoneal fascia, or can come away with the peritoneum. Alternatively, part of the properitoneal fat layer can remain attached to the peritoneum and part of the fat layer can come away attached to the peritoneum. Because of the uncertainty in the point of separation, the layer which is detached will be called the peritoneum, and the layer from which the peritoneum is detached will be called the underlying layer.

Additional layers of tissue lie between the properitoneal fascia and the skin S.

An inguinal hernia occurs when the contents of the abdominal cavity break through the abdominal wall. As described above, a hernia is repaired by attaching a piece of mesh to the abdominal wall. To prevent the mesh from causing trauma to the bowel, either through irritation of the bowel by the rough surface of the mesh, or by adhesion of the bowel to the mesh, it is preferred to attach the mesh to the properitoneal fascia. With the mesh attached to the fascia, the peritoneum covers the mesh and isolates the bowel from the mesh.

Conventional techniques of attaching the mesh patch to the properitoneal fascia, both laparoscopic and normal, involve blunt dissecting the peritoneum away from the properitoneal fascia, working from inside or outside the belly. The apparatus and methods according to the invention enable the peritoneum to be separated from the properitoneal fascia and the mesh patch attached to the fascia without entering the belly.

Although the following description will describe the apparatus and methods according to the invention with respect to hernia repair, the apparatus and methods are not restricted to hernia repair. The apparatus and methods can equally well be used in other procedures in which one layer of tissue is separated from another to form a working space between the layers. These procedures include thoracoscopy in patients with pleural adhesions; pericardioscopy, or the introduction of an endoscope into the pericardial cavity, in patients with pericardial adhesions; retroperitoneal lymph node dissection, in which the peritoneum on the distal aspect of the abdominal cavity is separated from the underlying tissue which includes lymph nodes; and in separating a blood vessel from surrounding connective tissue in the course of, for example, a femoropopliteal arterial bypass graft procedure.

1. TWO-COMPONENT APPARATUS AND METHOD OF USING

The two-component form of the apparatus according to the invention is shown in FIGS. 2A through 2C. FIG. 2A shows a partially cut-away view of the separation component 1 of the apparatus. In the separation component, the introducer tube 3 is a rigid tube having a bore with a circular cross section that can accommodate an endoscope.

The proximal end of the introducer tube is fitted with a port 5, in the proximal end 7 of which is mounted a flapper valve 2. The shutter 6 of the flapper valve is operated by the button 9. The seat 4 of the flapper valve additionally forms a gas-tight seal with an endoscope or other instrument inserted though the flapper valve into the bore of the introducer tube 3. The port 5 is also fitted with a valve 11 to which a supply of a suitable inflation fluid can be connected.

The main envelope 12 defines a main inflatable chamber 13. The main envelope is fitted to the distal end 15 of the introducer tube 3. The main envelope and main inflatable chamber are shown in their collapsed states. The dotted line 12X indicates the extent of the main envelope when the main inflatable chamber 13 in its expanded state.

The main envelope 12 is preferably formed from an elastomeric material, such as latex, silicone rubber, or polyurethane. The main envelope can also be formed from a thin, inelastic material such as Mylar®, polyethylene, nylon, etc. If an inelastic material is used, it should be suitably packaged to fit inside the bore of the introducer tube 3 when in its collapsed state.

The preferred elastomeric main envelope 12 can be simply attached to the distal end 15 of the introducer tube 3 by stretching the main envelope over the distal end of the introducer tube, as shown in FIG. 2B. The main envelope is then kept in place by friction resulting from the tension caused by stretching. A suitable adhesive, such as an epoxy or cyanoacrylate adhesive, may additionally or alternatively be used. Other means of attaching the main envelope to the inside or the outside of the introducer tube can be used.

After attachment, the main envelope 12 is inverted into the bore of the introducer tube, as shown in FIG. 2C. Inverting the main envelope into the bore of the introducer tube makes it easier to use the introducer tube to pass the main envelope through an incision and place it adjacent to the peritoneum, as will be described next.

The first pan of a method according to the invention of using the separation component 1 of a two-component apparatus according to the invention to separate a first layer of tissue from a second layer of tissue will next be described. As an illustration, separating the peritoneum from the properitoneal fascia in the course of repairing a hernia will be described.

Figure 3A:
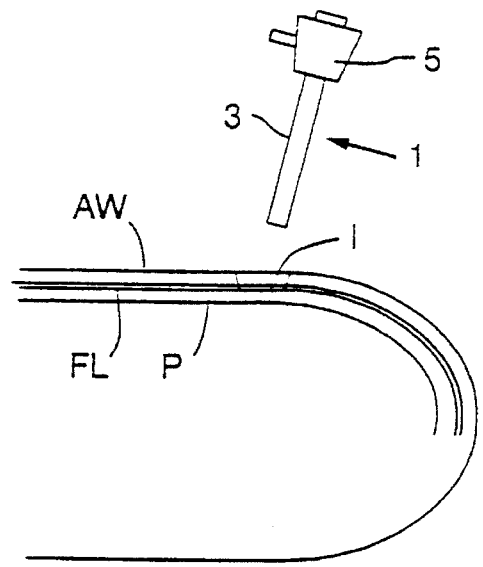
Figure 3B:
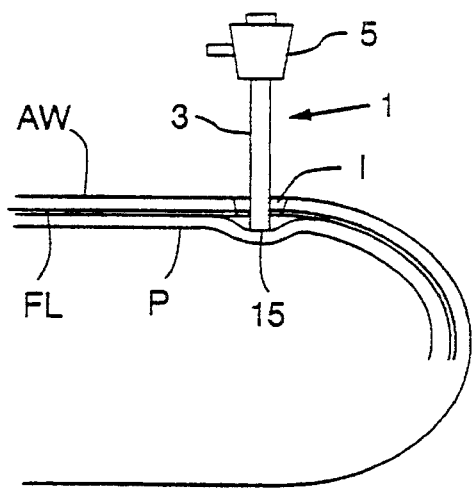

FIGS. 3A through 3H show a longitudinal cross section of the lower abdomen. An incision about 12–15 mm. long is made in the abdominal wall AW, and is carried through the abdominal wall as far as, and including, the properitoneal fat layer FL The distal end 15 of the introducer tube 3 of the separation component 1 is then inserted into the incision to bring the distal end into contact with the peritoneum P. Additional gentle pressure detaches the pan of the peritoneum in the immediate vicinity of the incision from the underlying layer, as shown in FIG. 3B. FIG. 3B shows the peritoneum detached from the properitoneal fat layer FL The main envelope cannot be seen in these figures because it is inverted within the bore of the introducer tube 3.

A source of a suitable inflation fluid (not shown) is connected to the valve 11. A gas, preferably air, is the preferred inflation fluid, but other gases, such as carbon dioxide, can be used. A liquid, such as saline solution, can be used, but liquids are less preferable to gases because they change the optical properties of any endoscope inserted into the main inflatable chamber 13. The flow of inflation fluid is turned on., which ejects the main envelope 12 of the main inflatable chamber 13 from the bore of the introducer tube 3.

The inflation fluid progressively expands the main envelope 12, and hence the main inflatable chamber 13 defined by the main envelope, into an expanded state. The main envelope expands between the peritoneum and the properitoneal fascia, and gently and progressively detaches an increasing area of the peritoneum from the underlying layer as it expands. When the main envelope is in its expanded state, the main inflatable chamber is preferably about 4"–6" (100–150 mm) in diameter.

Figure 3C:
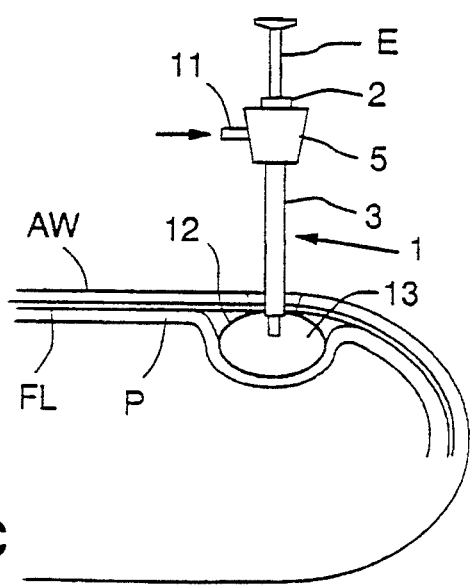

Early in the process of expanding the main envelope 12, an endoscope E is inserted into the flapper valve 2 in the port 5, as shown in FIG. 3C. The endoscope E is passed through the bore of the introducer tube 3 into the main inflatable chamber 13. Once partially expanded, the main envelope 12 is sufficiently transparent for the extent of the detachment of the peritoneum to be observed through the endoscope.

Figure 3D:
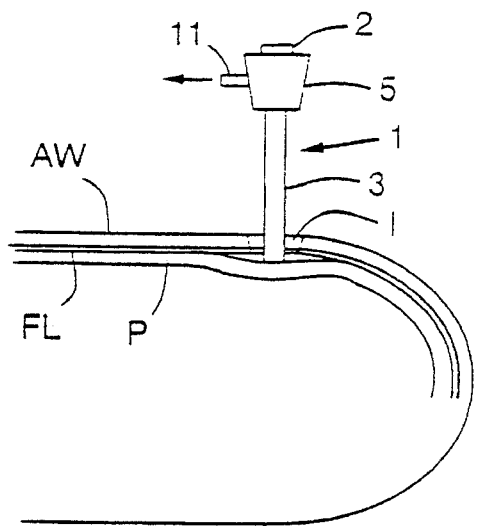
Figure 3E:
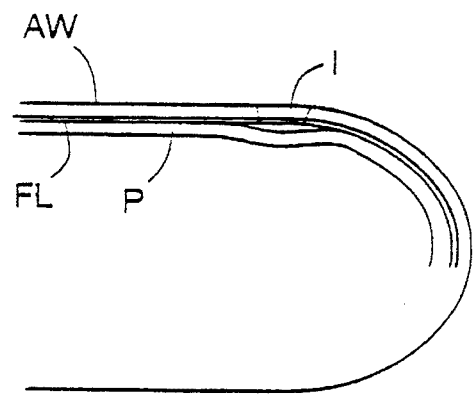

When a sufficient area of the peritoneum has been detached, the supply of inflation fluid is turned off. The inflation fluid is then vented from the main inflatable chamber, and the main envelope 12 progressively returns to its collapsed state. The peritoneum remains detached from the properitoneal fascia, however, as shown in FIG. 3D. The separation component 1, including the collapsed main envelope, is then withdrawn from the incision I (FIG. 3E).

The insufflation component 21 of the two-component apparatus, shown in FIG. 2D, will next be described. The insufflation component 21 comprises an inner tube 35 and an outer tube 37 mounted coaxially, with the outer tube covering the inner tube over most of the length of the inner tube. The inner tube is similar the introducer tube 3 (FIG. 2A), and is a rigid tube having a bore with a circular cross section that can accommodate a 10 mm endoscope.

The proximal end of the inner tube 35 is fitted with a port 25, the proximal end 27 of which has a flapper valve 32. The shutter 36 of the flapper valve is operated by the button 29. Additionally, the seat 34 of the flapper valve forms a gas-tight seal with an endoscope (not shown) or an obturator, such as the obturator 33, inserted though the flapper valve into the bore of the inner tube 35. The port 25 is also fitted with a first valve 31 to which a supply of a suitable insufflation fluid can be connected.

The distal end 41 of the outer tube 37 stops short of the distal end 39 of the inner tube 35. The insufflation component 21 includes a toroidal inflatable chamber 43. The envelope 45 of the toroidal inflatable chamber is a cylindrical piece of a thin elastomeric material, such a latex, silicone rubber, or polyurethane. The envelope 45 is placed over the distal ends of the inner tube and the outer tube. The proximal end 47 of the envelope is attached to the distal end 41 of the outer tube, and the distal end 49 of the envelope is attached to the distal end 39 of the inner tube 35.

The bore of the outer tube 37 is spaced from the outer surface of the inner tube 35. The annular space 51 between the inner tube and the outer tube interconnects the toroidal inflatable chamber 43 and a second valve 53. The second valve 53 is connected to a source of a suitable inflation fluid (not shown). Thus, the toroidal inflatable chamber 45 can be inflated using an inflation fluid passing into the toroidal inflatable chamber via the second valve 53 and the annular space 51. The toroidal inflatable chamber is shown in its collapsed state in FIG. 2D, and in its expanded state in FIG. 2E.

The anchor flange 55 is slidably mounted on the outer tube 37, and can be locked in a desired position along the length of the outer tube with a simple over-center action locking lever (not shown). As will be described in detail below, the anchor flange and the toroidal inflatable chamber, in its expanded condition, enable the insufflator component 21 to form a gas-tight seal to prevent insufflation gas passed through the insufflator component from escaping.

The use of the insufflation component 21 in the second pan of the method according to the invention of using the two-component apparatus according to the invention will next be described.

Figure 3F:
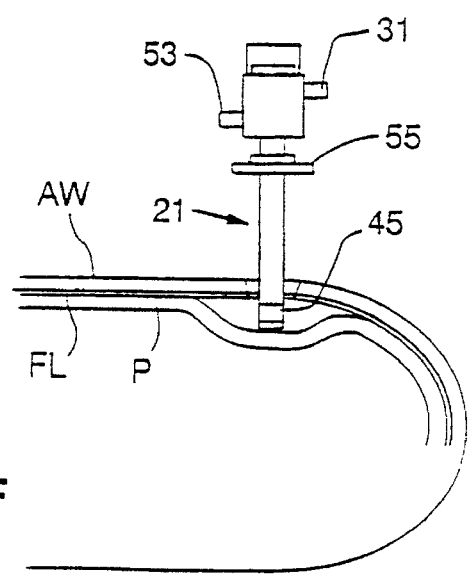

An obturator 33, having a blunt tip 59, is preferably inserted through the flapper valve 32 in the port 25 into the bore of the inner tube 35. The tip of the obturator projects beyond the distal end of the inner tube to provide the insufflation component 21 with a blunt nose. The blunt nose enables the distal end of the insufflation component to be atraumatically inserted into the properitoneal space through the incision I. The insufflation component is advanced through the incision until the proximal end of the cylindrical envelope 45 is in the properitoneal space, clear of the incision, as shown in FIG. 3F.

Figure 3G:
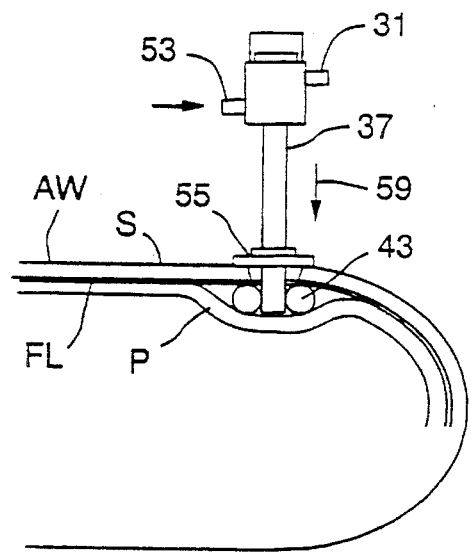

A suitable source (not shown) of an inflation fluid is attached to the second valve 53. A gas, such as air or carbon dioxide, can be used for the inflation fluid; alternatively, a liquid, such as saline can be used. Since the volume of inflation fluid required to inflate the toroidal inflatable chamber is small, about 15 ml in the preferred embodiment, the inflation fluid can be forced into the toroidal inflatable chamber from a large syringe. Inflation fluid is fed into the toroidal inflatable chamber 43 to expand the toroidal inflatable chamber to its expanded condition, as shown in FIG. 3G.

The anchor flange 55 is then advanced in the direction of the arrow 59 along the outer tube 37 to bring the anchor flange into contact with the skin S of the abdominal wall AW. The insufflation component 21 is then gripped, and the anchor flange is further advanced slightly. This forces the expanded toroidal inflatable chamber 43 into contact with the underlying layer, and slightly compresses the abdominal wall, including the underlying layer, but excluding the peritoneum P, between the toroidal inflatable chamber and the anchor flange. Once adjusted, the anchor flange is locked in position on the outer tube. The expanded toroidal inflatable chamber is held against the underlying layer, and forms a gas-tight seal between the insufflation component and the abdominal wall, including the underlying layer, excluding the peritoneum.

Figure 3H:
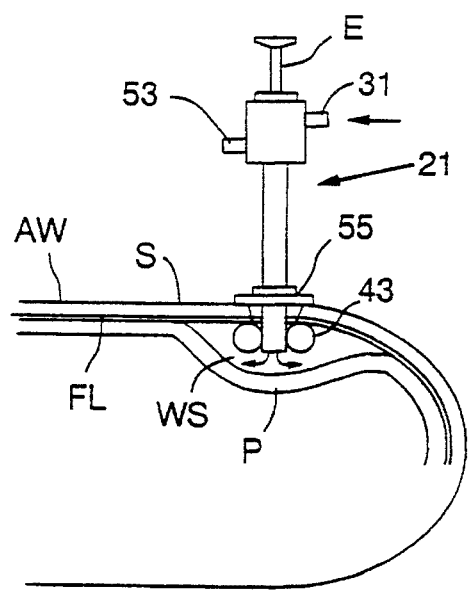

A suitable source (not shown) of an insufflation gas is attached to the first valve 31, and insufflation gas is passed through the bore of the inner tube 35 into the working WS space between the peritoneum P and the underlying layer created by separating by the peritoneum from the underlying layer using the separation component of the apparatus in the first pan of the method described above. The pressure of the insufflation gas re-separates the peritoneum from the underlying layer, as shown in FIG. 3H, and provides a working space in which repair of the hernia can be carried out. The obturator is removed from the bore of the inner tube 35. The bore of the inner tube 35 can then be used to pass instruments, such as the endoscope E, into the working space to perform the repair procedure. Insufflation pressure is maintained by the flapper valve 32.

Figure 3I:
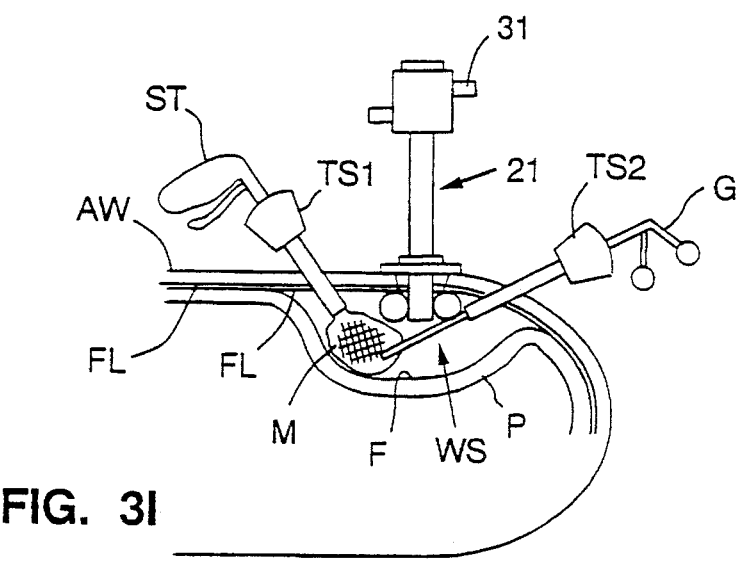

As pan of the hernia repair procedure, additional gas-tight trocar sheaths are inserted through the abdominal wall into the working space WS, as shown in FIG. 3I. An endoscope (not shown) can be passed into the working space through the bore of the inner tube 35, or through one of the additional trocar sleeves for observation. If the properitoneal fat layer FL remains attached to the properitoneal fascia F, it is scraped off the fascia around the site of the hernia so that the patch can be attached directly to the fascia.

A patch M, preferably a Dacron® or Teflon® mesh, is shown gripped by the grippers G, and passed through the trocar sleeve TS2 into the working space. Using the grippers, the patch is manipulated to place it in contact with the properitoneal fascia F over the site of the hernia. The patch is attached to the properitoneal fascia by staples inserted using the stapler ST passed through the trocar sleeve TS1 into the working space. Sutures can alternatively be used to attach the patch to the properitoneal fascia.

After the treatment procedure is completed, the first valve 31 is operated to release the insufflation gas from the working space. The second valve 53 is operated to release the inflation fluid from the toroidal inflatable chamber 43. The envelope 45 of the toroidal inflatable chamber returns to its collapsed state, flush with the outer surfaces of the inner tube and the outer tube. The insufflating component is then withdrawn from the incision, and the incision is closed using sutures or clips. The pressure of the viscera against the peritoneum returns the peritoneum into contact with the underlying layer. Over time, the peritoneum reattaches to the underlying layer.

2. FIRST ONE-COMPONENT APPARATUS (a) Main Embodiment

The separation component can be dispensed with, and the insufflation component can be modified to provide the first embodiment of a one component apparatus according to the invention. The first one-component apparatus is shown in FIG. 4A. The first one-component apparatus 121 is similar to the insufflation component just described. Like components will use the same reference numbers with 100 added. The first one component apparatus comprises a tube assembly 160, including an inner tube 135 coaxially mounted inside an outer tube 137. The outer tube covers the inner tube over most of the length of the inner tube. The inner tube is a rigid tube having a bore with a circular cross section that can accommodate an endoscope (not shown).

The proximal end of the inner tube 135 is fitted with a port 125, the proximal end 127 of which includes a flapper valve 132. The shutter 136 of the flapper valve is operated by the button 129. Additionally, the seat 134 of the flapper valve forms a gas-tight seal with an endoscope (not shown), or other instrument, inserted though the flapper valve into the bore of the inner tube 135. The port 125 is also fitted with a first valve 131 to which a supply of a suitable insufflation fluid can be connected.

Unlike the insufflator component of the two-component apparatus, the distal end 141 of the outer tube 137 extends as far as the distal end 139 of the inner tube 135. The tubes are connected together over a distal portion 167 of their lengths (see detail in FIG. 4B). A circumferential groove 169 is formed in the inner wall of the distal portion 167. A groove with a wedge-shaped cross section is shown. The circumferential groove can have other cross sections, such as square, or semi-circular. The circumferential groove retains the main envelope 112, which defines the main inflatable chamber 113, in the bore of the inner tube, as will be described in more detail below.

The envelope 145 of the toroidal inflatable chamber 143 covers the distal part of the tube assembly 160. The envelope 145 is a cylindrical piece of a thin elastomeric material, such a latex, silicone rubber, or polyurethane. The proximal end 147 and the distal end 149 of the envelope are attached to the outer surface 163 of the tube assembly using a circumferential line of adhesive applied at each end of the envelope. An epoxy or cyanoacrylate adhesive is preferably used. When the toroidal inflatable chamber is in its collapsed state, the envelope 145 lies almost flush with the outer surface of the tube assembly 160.

The outer tube 137 is spaced from the inner tube 135 over at least part of its circumference. The space 151 between the inner tube and the outer tube, and a radial passage 161 through the wall of the outer tube interconnect the toroidal inflatable chamber 143 and the second valve 153. The second valve 153 is connected to a source of a suitable inflation fluid (not shown). The toroidal inflatable chamber is shown in its collapsed state in FIGS. 4A and 4B, and in its expanded state in FIG. 4C.

The anchor flange 155 is slidably mounted on the tube assembly 160, and can be locked in a desired position along the length of the tube assembly with a simple over-center action locking lever (not shown). As will be described in detail below, the anchor flange and the toroidal inflatable chamber, in its expanded condition, form a gas-tight seal to prevent insufflation gas from escaping.

The first one-component apparatus also includes a main envelope 112 detachably attached to the bore of the inner tube 135. The main envelope defines the main inflatable chamber 113. The main envelope is preferably formed of an elastomeric material such as latex, silicone rubber, or polyurethane. The main envelope can also be formed from a thin, inelastic material such as Mylar®, polyethylene, nylon, etc. If an inelastic material is used, it should be suitably packaged to fit inside the bore of the inner tube when in its collapsed state.

The main envelope 112 is formed such that it has a substantially spherical shape when it is in its expanded state, and is also formed with a neck 165. The neck has an outside diameter substantially equal to the diameter of the bore of the inner tube 135. The neck 165 can be rolled outwards a number of times, as in the neck of a common toy balloon, or the neck can be attached to a suitable O-ring 171, as shown in FIG. 4B. The rolled neck, or the O-ring attached to the neck, engages with the circumferential groove 169 in the inner wall in the inner tube to attach the main envelope 112 to the inner tube. The main envelope is housed in the bore of the inner tube when the main inflatable chamber is in its collapsed state.

The rip cord 173 is attached to the neck 165 of the main envelope 112, runs proximally up the bore of the inner tube 135, and emerges from the port 125 through the flapper valve 132. The pan of the rip cord 173 emerging from the flapper valve can be gripped and pulled in a proximal direction to release the rolled neck 165 or the O-ring 171 from the circumferential groove 169. By pulling further on the rip cord, the entire main envelope can be pulled proximally through the bore of the inner tube.

(b) Alternative Embodiment

Figure 5A:
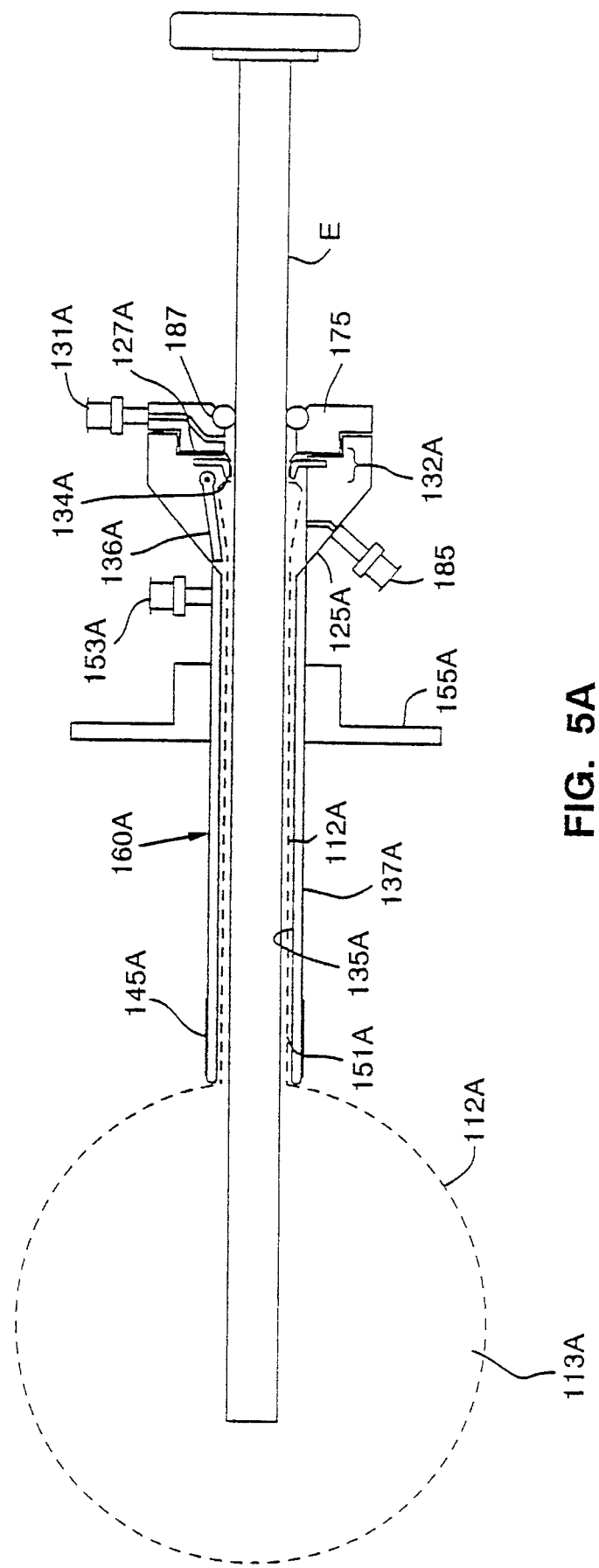

An alternative embodiment of the first one-component apparatus having an elongated main envelope 112A is shown in FIG. 5A. The tube assembly 160A includes the inner tube 135A mounted coaxially inside the outer tube 137A, with the proximal and distal ends of the tubes interconnected. The space 151A between the inner tube and the outer tube communicates with the toroidal inflatable chamber through the radial passage 161A in the wall of the outer tube. The space between the inner tube and the outer tube also communicates with the toroidal chamber inflation valve 153A.

The bore of the inner tube 135A communicates with the port 125A, fitted with the insufflation valve 185. The port 125A is also fitted with a flapper valve 132A, including the flapper valve seat 134A, which maintains gas pressure when the apparatus is used for insufflation. The flapper valve seat 134A also provides a gas-tight seal around any instrument, such as the endoscope E, passed through the flapper valve.

The elongated main envelope 112A is shown in FIG. 5B. The main envelope is an elongated cylinder with a dosed distal end 177. The main envelope is preferably formed from an elastomeric material, such as latex, silicon rubber, or polyurethane. Attached to the proximal end of the main envelope is a manifold 175 which mates with the proximal face 127A of the port 125A. The manifold 175 is fitted with an O-ring seal 187, which forms a gas-tight seal with any instrument passed through it. The manifold 175 is also fitted with the main chamber inflation valve 131A to which a supply (not shown) of a suitable inflation fluid can be attached to inflate the main inflatable chamber 112A.

The elongated main envelope 112A is passed through the flapper valve 132A into the bore of the inner tube 135A. The manifold 175 is engaged with the proximal face 127A of the port 125A. When the manifold is engaged, the distal end 177 of the main envelope projects beyond the distal end of the tube assembly 160& as shown in FIG. 5C. The distal end of the main envelope is then inverted into the bore of the inner tube 135A, as shown in FIG. 5D.

An endoscope, or some other suitable instrument, is inserted through the O-ring seal 187 to seal the manifold before inflation fluid is passed through the main chamber inflation valve 131A to inflate the main inflatable chamber 113A.

Alternatively, the seal 187 can be replaced by an additional flapper valve (not shown) so that the main inflatable chamber can be inflated without the need to use an instrument to seal the manifold.

When inflation fluid is passed into the main inflatable chamber 113A through the valve 131A, the distal end 177 of the main envelope 112A is ejected from the inner tube 135A. The inflation fluid then progressively expands the main envelope 112A, and hence the main inflatable chamber 113A defined by the main envelope, into an expanded state, as shown in FIG. 5A. The pan of the main envelope inside the inner tube is subject to the same inflation pressure as the distal end 177 of the main envelope, but is constrained by the inner tube and so does not inflate.

After using the main envelope 112A to separate the peritoneum away from the underlying layer, as will be described in detail below, the inflation pressure fluid is vented from the main inflatable chamber 113A, and the main envelope returns to its collapsed state. When the main envelope is in its collapsed state, it can move freely in the bore of the inner tube 135. The main envelope is removed from the inner tube by disengaging the manifold 175 from the proximal face 127A of the port 125A, and using the manifold 175 to pull the main envelope proximally through the bore of the inner tube.

Inflation fluid for the toroidal inflatable chamber the envelope of which 145A is shown in FIG. 5A, is passed through the toroidal chamber inflation valve 153A. Insufflation gas is passed through the insufflation valve 185.

The toroidal inflatable chamber and the anchor flange 155A of the alternative embodiment of the first one-component apparatus are the same as in the main embodiment, and will therefore not be described.

(c) Method of Using the First One-Component Apparatus (Both Forms)

The method according to the invention of using either form of the first one-component apparatus according to the invention to separate a first layer of tissue from a second layer of tissue will next be described. As an illustration, separating the peritoneum from the properitoneal fascia in the course of repairing a hernia will be described.

Figure 6A:
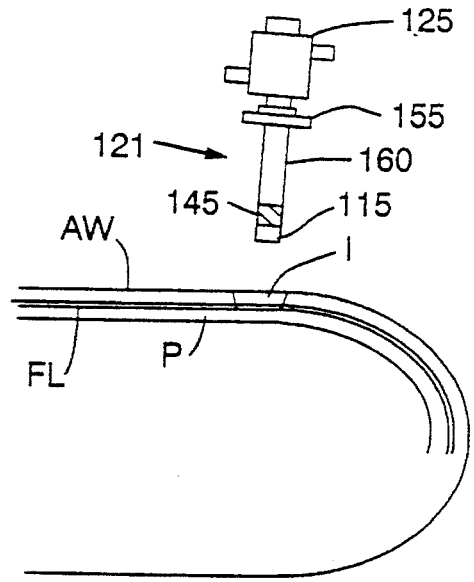
Figure 6B:
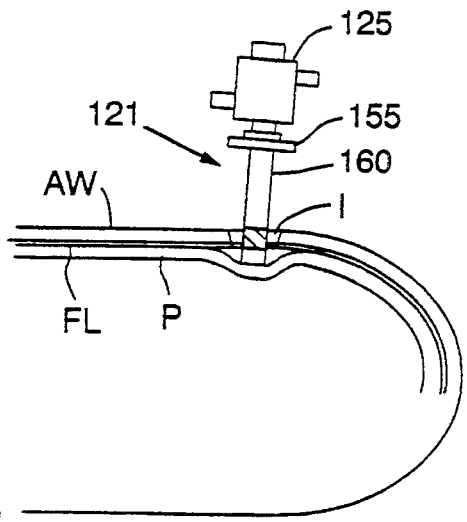

FIGS. 6A through 6H show a longitudinal cross section of the lower abdomen. An incision about 12–15 mm. long is made in the abdominal wall AW, and carried through the abdominal wall as far as, and including the properitoneal fat layer FL, as shown in FIG. 6A. The distal end 115 of the tube assembly 160 of the one-component apparatus 121 is then inserted into the incision to bring the distal end into contact with the peritoneum. Additional gentle pressure detaches the part of the peritoneum in the immediate vicinity of the incision from the underlying layer, as shown in FIG. 6B. FIG. 6B shows the peritoneum detached from the properitoneal fat layer FL. The main envelope cannot be seen in these figures because it is inverted within the bore of the tube assembly.

A source of inflation fluid (not shown) is connected to the valve 131. A gas, preferably air, is the preferred inflation fluid, but other gases, such a carbon dioxide can be used. A liquid, such as saline solution can be used, but liquids are less preferable to gases because they change the optical properties of any endoscope inserted into the main inflatable chamber 113. The flow of inflation fluid is turned on, which ejects the main envelope 112 from the bore of the tube assembly 160.

The inflation fluid progressively expands the main envelope 112, and hence the main inflatable chamber 113 defined by the main envelope, into an expanded state. The main envelope expands between the peritoneum P and the properitoneal fat layer FL, and gently and progressively detaches an increasing area of the peritoneum from the underlying layer as it expands. When the main envelope is in its expanded state, the main inflatable chamber is preferably about 4"–6" (100–150 mm) in diameter.

Figure 6C:
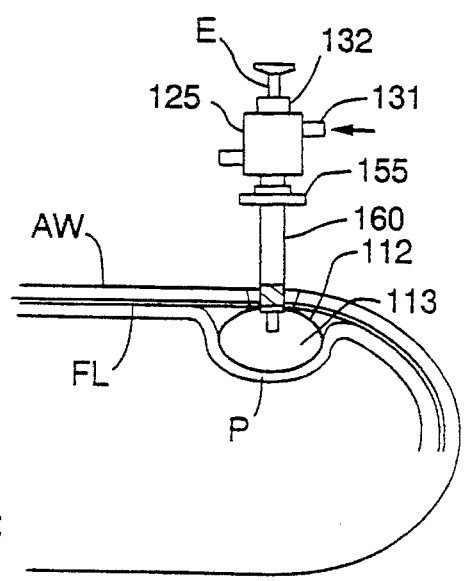

Early in the process of expanding the main envelope 112, an endoscope E is inserted into the flapper valve 132 in the port 125, as shown in FIG. 6C. The endoscope E is passed through the bore of the tube assembly 160 into the main inflatable chamber 113. Once the partially expanded, the main envelope is sufficiently transparent for the extent of the detachment of the peritoneum to be observed using the endoscope.

Figure 6D:
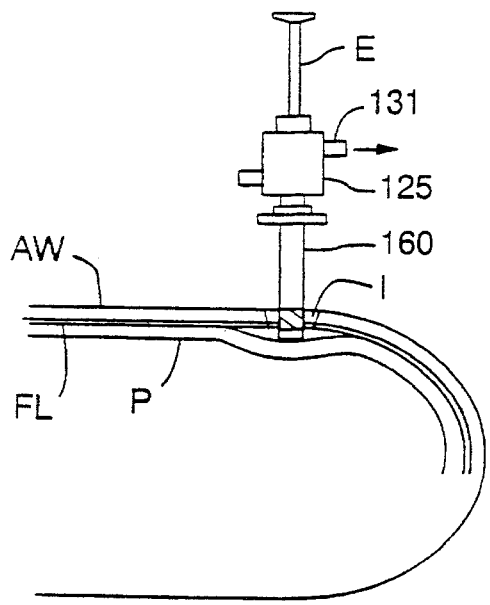

When a sufficient area of the peritoneum is detached, the supply of inflation fluid is turned off. The inflation fluid is then vented from the main inflatable chamber 113, and the main envelope progressively returns to its collapsed state. The peritoneum remains detached from the underlying layer, however, as shown in FIG. 6D. The main envelope is then removed from the bore of the tube assembly 160. The different methods of removing the main envelope from the bore of the tube assembly for the two different forms of the first one-component apparatus are described above.

Figure 6E:
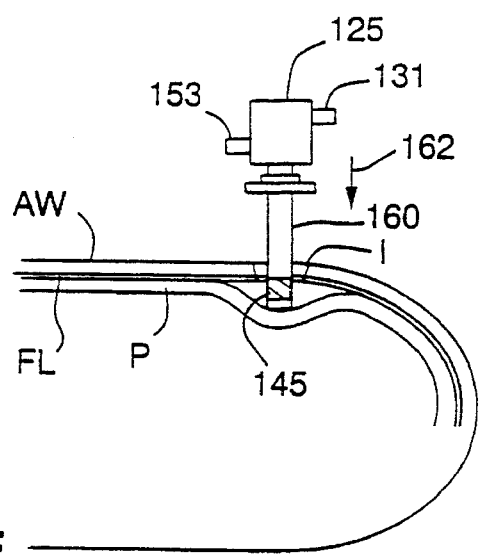

After the main envelope 112 has been removed from the bore of the tube assembly, the tube assembly is advanced into the incision in the direction of the arrow 162 until the proximal end of the envelope 145 of the toroidal inflatable chamber is in the properitoneal space, clear of the incision, as shown in FIG. 6E.

Figure 6F:
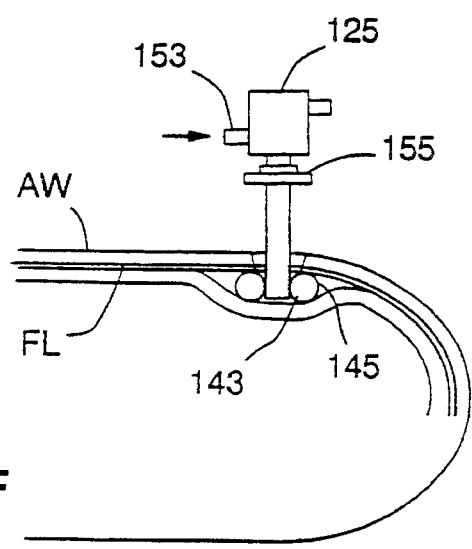

A suitable source (not shown) of an inflation fluid is attached to the valve 153. A gas, such as air or carbon dioxide, can be used for the inflation fluid; alternatively, a liquid, such as saline can be used. Since the volume of inflation fluid required to inflate the toroidol inflatable chamber is small, about 15 ml in the preferred embodiment, the inflation fluid can be contained in a large syringe. Inflation fluid is fed into the toroidal inflatable chamber 43 to expand the toroidal inflatable chamber to its expanded condition, as shown in FIG. 6F.

Figure 6G:
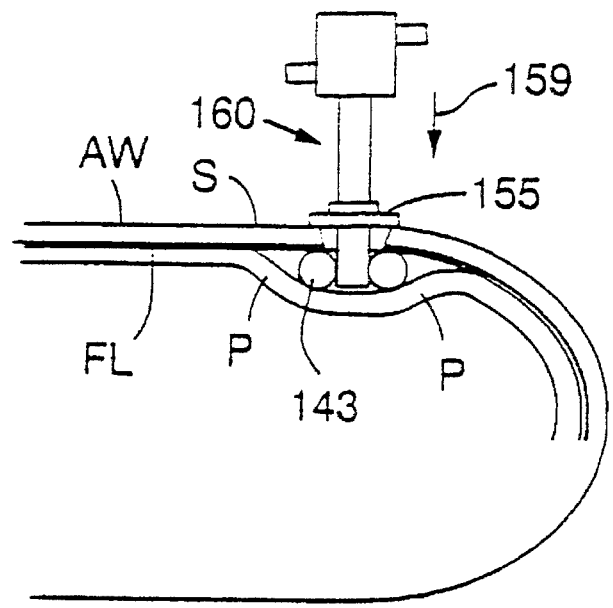

The anchor flange 155 is then advanced in the direction of the arrow 159 along the tube assembly 160 to bring the anchor flange into contact with the skin S of the abdominal wall AW. The tube assembly 160 is then gripped, and the anchor flange is further advanced slightly. This forces the expanded toroidal inflatable chamber 143 into contact with the underlying layer, and slightly compresses the abdominal wall AW, including the underlying layer but excluding the peritoneum P, between the expanded toroidal inflatable chamber and the anchor flange, as shown in FIG. 6G. Once adjusted, the anchor flange is locked in position on the tube assembly. The expanded toroidal inflatable chamber is held against the underlying layer and forms a gas-tight seal with the abdominal wall, excluding the peritoneum.

Figure 6H:
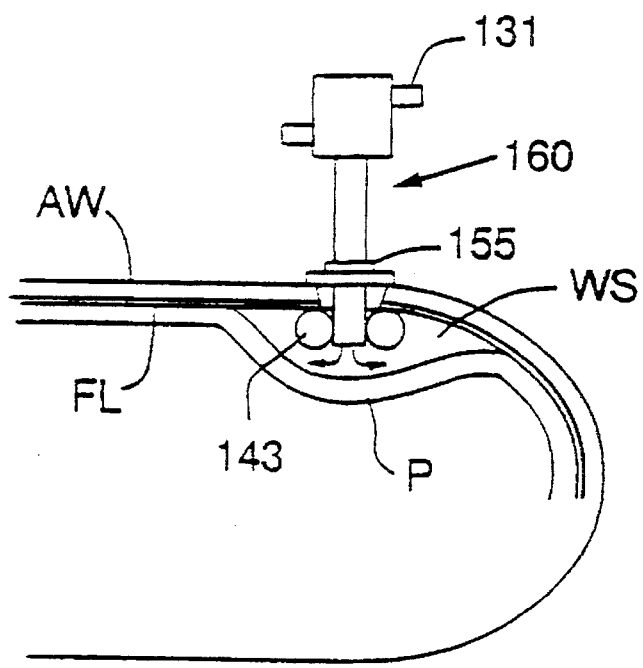

A suitable source (not shown) of an insufflation gas is attached to the first valve 131, and insufflation gas is passed through the bore of the inner tube 135 into the working space WS between the peritoneum P and the underlying layer created by separating the peritoneum from the underlying layer. The pressure of the insufflation gas re-separates the peritoneum from the underlying layer, as shown in FIG. 6H, and provides a working space in which repair of the hernia can be carried out. The bore of the tube assembly 160 can be used to pass instruments, such as the endoscope E, into the working space to perform the repair procedure. When no instrument is inserted into the bore of the tube assembly, insufflation pressure is maintained by the flapper valve.

As pan of the hernia repair procedure, additional gas-tight trocar sleeves (not shown) are inserted through the abdominal wall into the working space. The same procedure as described above in connection with FIG. 3I is used to attach a mesh patch to the properitoneal fascia over the site of the hernia. The process can be observed with the aid of an endoscope (not shown) passed through the bore of the tube assembly 160, or through one of the additional trocar sleeves.

After the treatment procedure is completed, the valve 131 is operated to release the insufflation gas from the working space WS. The valve 153 is operated to release the inflation fluid from the toroidal inflatable chamber 143, which releases compression of the abdominal wall AW, excluding the peritoneum. The toroidal inflatable chamber returns to its collapsed state, with its envelope 145 flush with the outer surface the tube assembly 160. The tube assembly is then withdrawn from the incision, and the incision is closed using sutures or dips. The pressure of the viscera against the peritoneum returns the peritoneum into contact with the underlying layer. Over time, the peritoneum reattaches to the underlying layer.

3. SECOND ONE-COMPONENT APPARATUS (a) Second One-Component Apparatus

A second embodiment of a one-component apparatus is shown in FIGS. 7A and 7B. The second one-component apparatus 121 is similar to the first one-component apparatus just described. However, the second one-component apparatus has a substantially spherical toroidal main inflatable chamber, that avoids the need to detach and remove the main envelope at the end of the separation process. Also, in the second one-component apparatus, a single toroidal main inflatable chamber provides the separating function of the main inflatable chamber and the sealing function of the toroidal inflatable chamber of the first one-component apparatus.

In the following description, similar components will use the same reference numbers with an additional 1130 added.

The second one-component apparatus comprises a tube assembly 260, including an outer tube 237 to which is attached a twin port assembly 224 is attached. The port assembly includes a first port 226 and a second port 228. The first port is provided with a first flapper valve 202, including the flapper valve seat 204. The second port is provided with a second flapper valve 206, including the flapper valve seat 208. Each flapper valve seat additionally forms a gas-tight seal with an instrument passed through it.

The tube assembly 260 also includes the inner tube 235. The inner tube has a length that is shorter than the length of the outer tube 237. The proximal end 210 of the inner tube is flexibly attached to the proximal end 222 of the outer tube 237 and to the first port 226. The flexible attachment enables the distal end 214 of the inner tube to move in the direction shown by the arrow 216. The first port communicates with the bore of the inner tube 235, and the second port communicates with the bore of the outer tube 237.

The insufflation valve 285 communicates with the first port 226, and the bore of the inner tube 235. The main chamber inflation valve 231 communicates with the second port 228, and the bore of the outer tube 237.

The main envelope 212 defines the main inflatable chamber 213 and comprises a cylindrical piece of an elastomeric material such a latex, silicone rubber, or polyurethane. The apparatus is shown with its main envelope in its collapsed state in FIG. 7B, in which the structure of the main envelope can also be seen. The main envelope preferably has a diameter smaller than the outside diameter of the inner tube. One end 230 of the main envelope is attached to the distal end 214 of the inner tube 235 by means of a suitable adhesive, such as an epoxy or cyanoacrylate adhesive. The other end 232 of the main envelope is evened (i.e., turned back on itself to bring the inside surface 234 of the main envelope to the outside) and attached to the distal end 236 of the outer tube using the same type of adhesive. The main envelope is preferably attached to the outer surfaces of the inner tube and the outer tube.

The apparatus is shown with the main envelope 212 in its expanded state in FIG. 7A. A suitable source of inflation gas is connected to the valve 231 and flows into the main inflatable chamber through the bore of the outer tube 237. The pressure acting on the surface 238 of the main envelope 212 causes the main envelope to assume the toroidal shape shown in FIG. 7A to define the toroidal main chamber 213. FIGS. 7A and 7B show the correspondence between the surfaces 234 and 238 of the main envelope when the main envelope is in its collapsed state (FIG. 7B) and in its expanded state (FIG. 7A).

The anchor flange 255 is slidably mounted on the tube assembly 260, and can be locked in a desired position along the length of the tube assembly. The anchor flange 255 is similar to the anchor flange 55 (FIG. 2A) and so will not be described further.

Figure 8A:
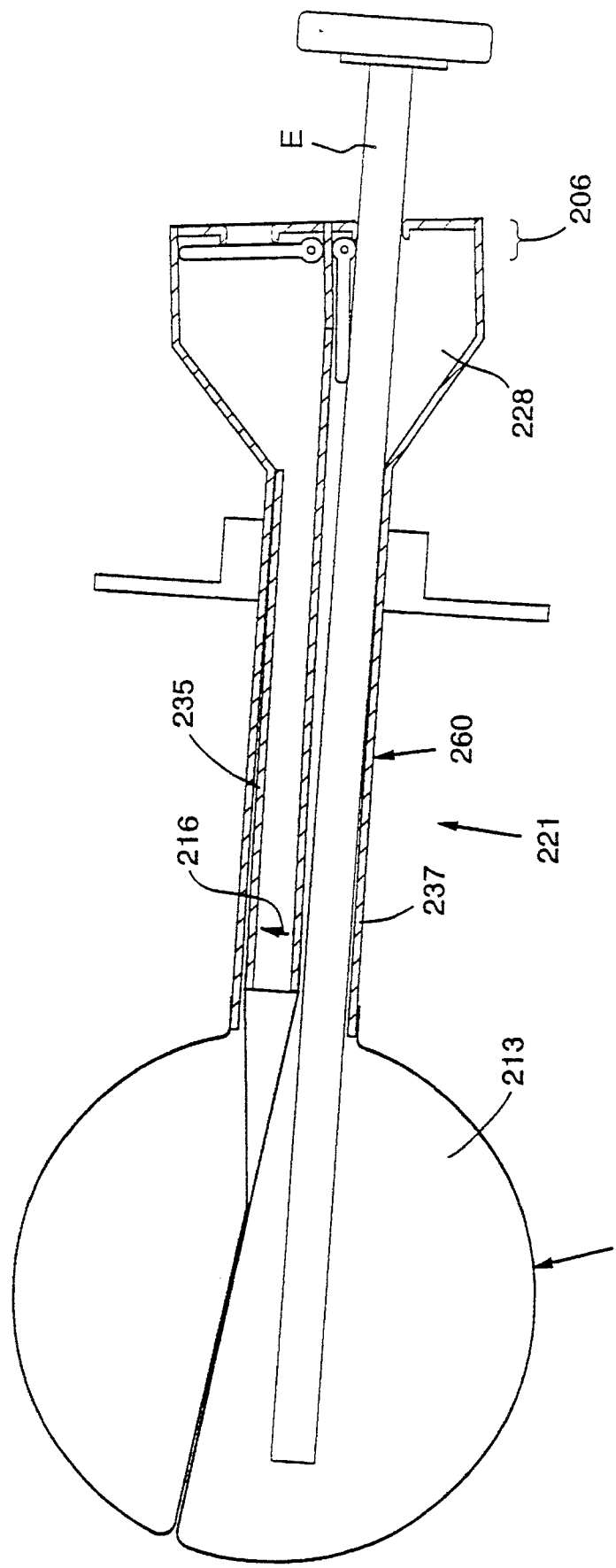
FIG. 8A shows the second one-component apparatus according to the invention with the main envelope in its expanded state and an endoscope passed through the bore of the outer tube into the main inflatable chamber.

In FIG. 8A, an endoscope E is shown passed through the second flapper valve 206, the second poll 228, and the bore of the outer tube 237 into the main inflatable chamber 213. The flexible mounting of the inner tube 235 in the outer tube enables the endoscope to displace the inner tube 235 in direction of the arrow 216 to gain access to the main inflatable chamber. The endoscope is inserted through the second port into the main inflatable chamber during the separation phase of using the apparatus to observe the extent of the separation of tissue.

Figure 8B:
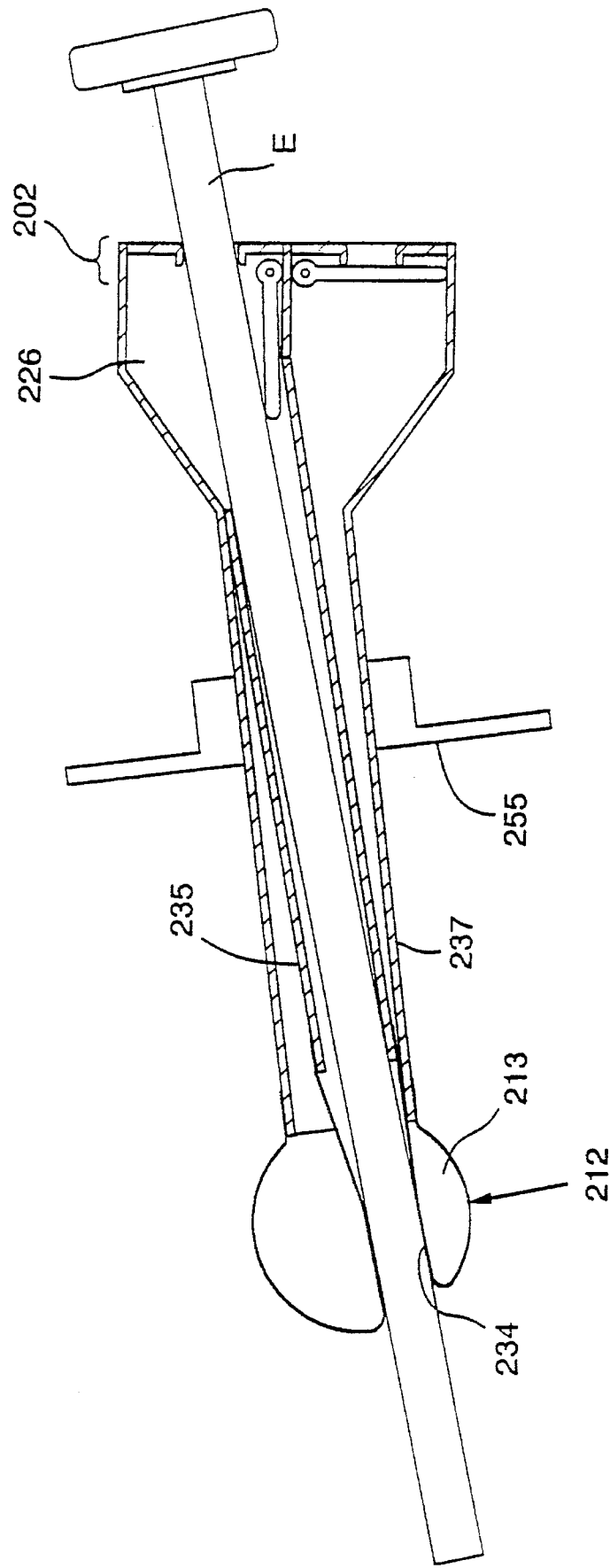
FIG. 8B shows the second one-component apparatus according to the invention with the main inflatable chamber in its partially expanded state and an endoscope passed through the bore of the inner tube and through the bore of the main envelope.

In FIG. 8B, an endoscope E is shown passed through the first flapper valve 202, the first port 226, the bore of the inner tube 235, and the bore 234 of the main envelope 212. The distal part of the endoscope emerges from the bore of the main envelope, and can be advanced beyond the main inflatable chamber 213 to observe the site of the hernia more closely. The endoscope is inserted through the first port, the inner tube, and the bore of the main envelope during the insufflation phase of using the apparatus. Instruments other than endoscopes can also be passed to the site of the hernia through the first flapper valve, the first port, the inner tube, and the bore of the main envelope if desired.

Also in FIG. 8B, the main envelope 212 is shown in the partially collapsed state that it preferably assumes during the insufflation phase of the procedure. In this pan of the procedure, the partially collapsed main inflatable chamber and the anchor flange 255 together provide a gas-tight seal to prevent the leakage of insufflation gas. Alternatively, this part of the procedure can be carried out with the main inflatable chamber in a fully expanded state.

(b) Method of Using the Second One-Component Apparatus

The method according to the invention of using the second embodiment of the one-component apparatus according to the invention to separate a first layer of tissue from a second layer of tissue will next be described. As an illustration, separating the peritoneum from the properitoneal fascia in the course of repairing a hernia will be described.

Figure 9A:
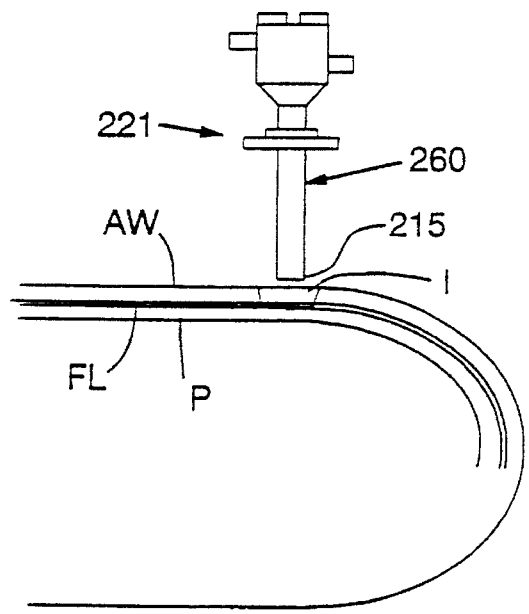
Figure 9B:
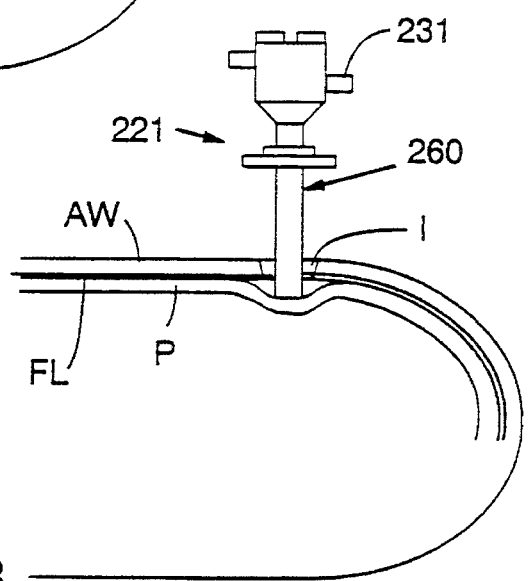

FIGS. 9A through 9F show a longitudinal cross section of the lower abdomen. An incision about 12–15 mm long is made in the abdominal wall AW, and carried through the abdominal wall as far as, and including, the properitoneal fat layer FL, as shown in FIG. 9A. The distal end 215 of the tube assembly 260 of the second one-component apparatus 221 is then inserted into the incision to bring the distal end into contact with the peritoneum P. Additional gentle pressure detaches the pan of the peritoneum in the immediate vicinity of the incision from the underlying layer, as shown in FIG. 9B. FIG. 9B shows the peritoneum detached from the properitoneal fat layer FL The main envelope cannot be seen in these figures because it is inverted within the bore of the tube assembly.

A source of inflation fluid (not shown) is connected to the valve 231. A gas, preferably air, is the preferred inflation fluid, but other gases, such a carbon dioxide can be used. A liquid, such as saline solution can be used, but liquids are less preferable to gases because they change the optical properties of any endoscope inserted into the main inflatable chamber. The flow of inflation fluid is turned on, which ejects the main envelope 212 from the bore of the tube assembly 260.

The Marion fluid progressively expands the main envelope 212, and hence the main inflatable chamber 213 defined by the main envelope, into an expanded state. The main envelope expands between the peritoneum P and the properitoneal fat layer FL, and gently and progressively separates an increasing area of the peritoneum from the underlying layer as it expands. When the main envelope is in its expanded state, the main inflatable chamber is preferably about 4"–6" (100–150 mm) in diameter.

Figure 9C:
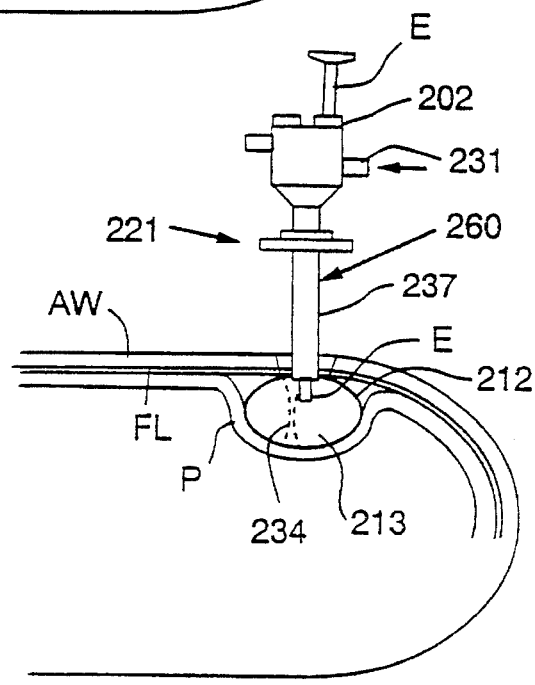

Early in the process of expanding the main envelope 212, an endoscope E is inserted into the first flapper valve 202, as shown in FIG. 9C. The endoscope E is passed through the bore of the outer tube 237 into the main inflatable chamber 213. Once partially expanded, the main envelope 212 is sufficiently transparent for the extent of the separation of the peritoneum to be observed using the endoscope.

Figure 9D:
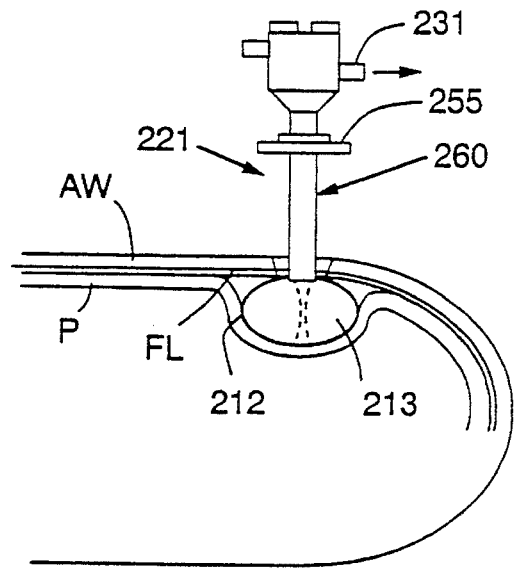

When a sufficient area of the peritoneum is separated, the supply of inflation fluid is turned off. The endoscope E is removed from the main inflatable chamber 213. The valve 231 is then opened to allow inflation fluid to vent partially from the main inflatable chamber 213. The main envelope 212 progressively returns part-way towards its collapsed state, as shown in FIG. 9D. Alternatively, the main envelope may be kept fully expanded.

Figure 9E:
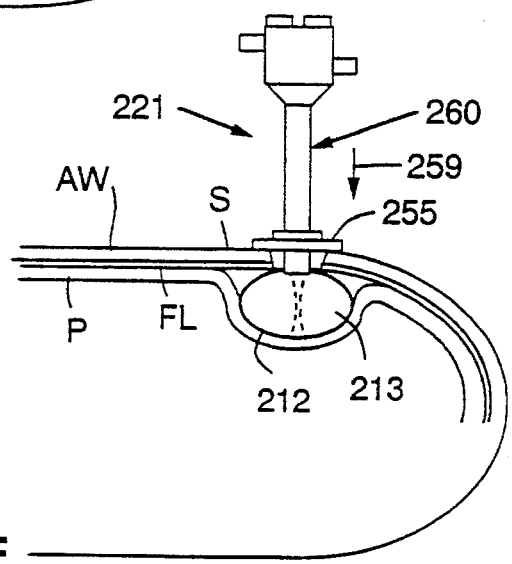

The anchor flange 255 is then advanced in the direction of the arrow 259 along the tube assembly 260 to bring the anchor flange into contact with the skin S of the abdominal wall AW. The tube assembly 260 is then gripped, and the anchor flange is further advanced slightly. This forces the main inflatable chamber 213 into contact with the underlying layer, and slightly compresses the abdominal wall, including the underlying layer but excluding the peritoneum, between the main inflatable chamber and the anchor flange, as shown in FIG. 9E. Once adjusted, the anchor flange is locked in position on the tube assembly. The main inflatable chamber is held against the underlying layer and forms a gas-tight seal with the abdominal wall, excluding the peritoneum.

Figure 9F:
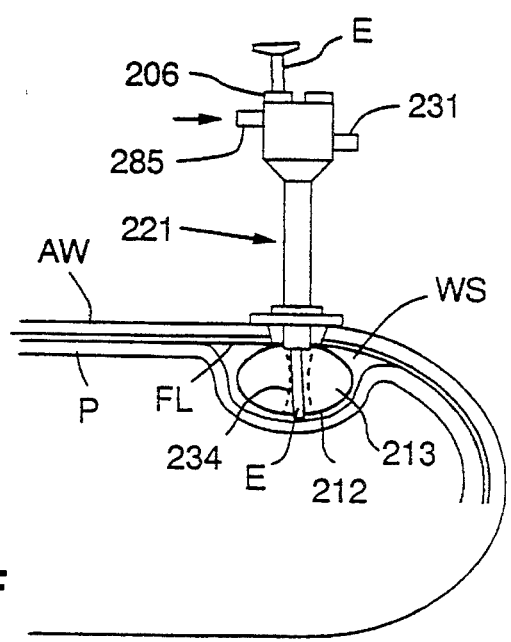

A suitable source (not shown) of insufflation gas is attached to the second valve 285, and insufflation gas is passed through the bore of the inner tube 235, and the bore 234 of the main envelope, into the working space WS between the peritoneum P and the underlying layer. The pressure of the insufflation gas re-separates the peritoneum from the underlying layer, as shown in FIG. 9F, and provides a working space in which repair of the hernia can be carried out.

Instruments, such as the endoscope E, can be passed through the second flapper valve 206, the bore of the inner tube 235, and the bore 234 of the main envelope, as shown in FIG. 8B, into the working space to perform the repair procedure. When no instrument is inserted into the bore of the inner tube, insufflation pressure is maintained by the second flapper valve.

As part of the hernia repair procedure, additional gas-tight trocar sleeves (not shown) are inserted through the abdominal wall into the working space. The same procedure as described above in connection with FIG. 3I is used to attach a mesh patch to the properitoneal fascia over the site of the hernia. The process can be observed with the aid of an endoscope (not shown) passed into the working space through the bore of the inner tube 235, or through one of the additional trocar sleeves.

After the treatment procedure is completed, the valve 285 is operated to release the insufflation gas from the working space. The valve 231 is operated to release the inflation fluid from the main inflatable chamber 213, which releases compression from the abdominal wall, excluding the peritoneum. The main envelope returns to its collapsed state inside the bore of the outer tube 237.

The tube assembly is then withdrawn from the incision, and the incision is closed using sutures or clips. The pressure of the viscera against the peritoneum returns the peritoneum into contact with the underlying layer. Over time, the peritoneum reattaches to the underlying layer.

4. HERNIA REPAIR METHOD WITH INCISION AT THE UMBILICUS

The hernia repair methods described so far show the incision placed close to the site of the hernia. In practice, it is preferred to make the incision at or near the umbilicus because the boundary between the peritoneum and the properitoneal fat layer can be more directly accessed near the umbilicus. The midline location of the umbilicus is devoid of muscle layers that would otherwise need to be traversed to reach the properitoneal fat layer.

Apparatus of the types described above inserted through an incision at the umbilicus would require a very large main inflatable chamber to detach the peritoneum from the umbilicus to the groin. Instead, in the method according to the invention to be described next, an apparatus of any one of the types described above is used to provide a tunnel from an incision at the umbilicus to the site of the hernia in the groin, and then to provide an insufflated working space at the site of the hernia.

The main envelope is partially expanded, collapsed, and advanced towards the site of the hernia. This sequence is repeated to progressively separate the peritoneum from the underlying layer and form the tunnel from the umbilicus to the site of the hernia. Then, at or near the site of the hernia, the main envelope is fully expanded to provide the working space at the site of the hernia. The working space is then insufflated to maintain the separation of the peritoneum from the underlying layer.

The following method can be practiced using the two-component embodiment of the apparatus, or any of the one-component embodiments of the apparatus. The method will be described using the two-component apparatus.

Figure 10A:
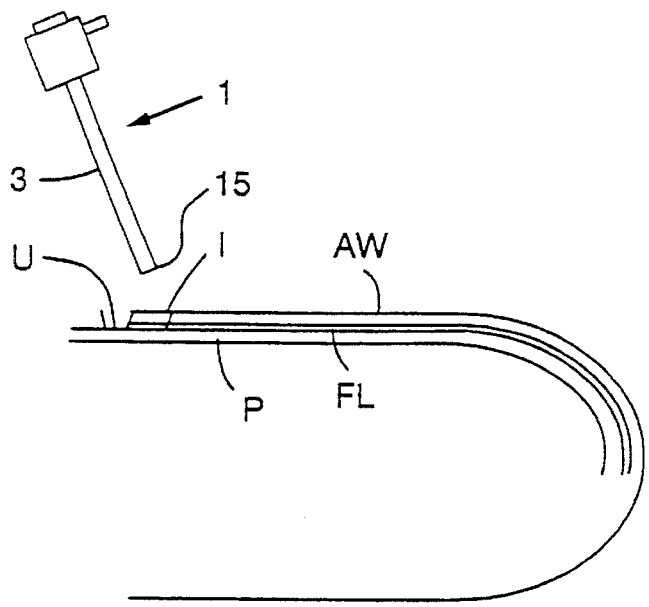
FIGS. 10A through 10I illustrate the alternative method according to the invention of using any of the apparatus according to the invention to separate the peritoneum from the underlying layer near the groin, with the apparatus inserted through an incision near the umbilicus.

An incision about 12–15 mm long is made in the abdominal wall AW, and is carried through the abdominal wall as far as, and including, the properitoneal fat layer FL. The incision is made at the umbilicus U, as shown in FIG. 10A.

Figure 10B:
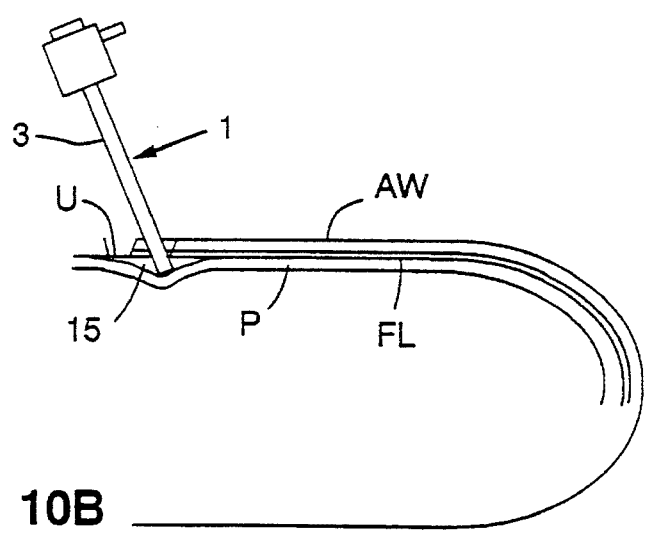

The distal end 15 of the introducer tube 3 of the separation component 1 is then inserted into the incision to bring the distal end into contact with the peritoneum P. Additional gentle pressure detaches the pan of the peritoneum in the immediate vicinity of the incision from the underlying layer, as shown in FIG. 10B. In FIG. 10B, the peritoneum is shown detached from the properitoneal fat layer FL The main envelope cannot be seen in these figures because it is inverted within the bore of the introducer tube 3.

Figure 10C:
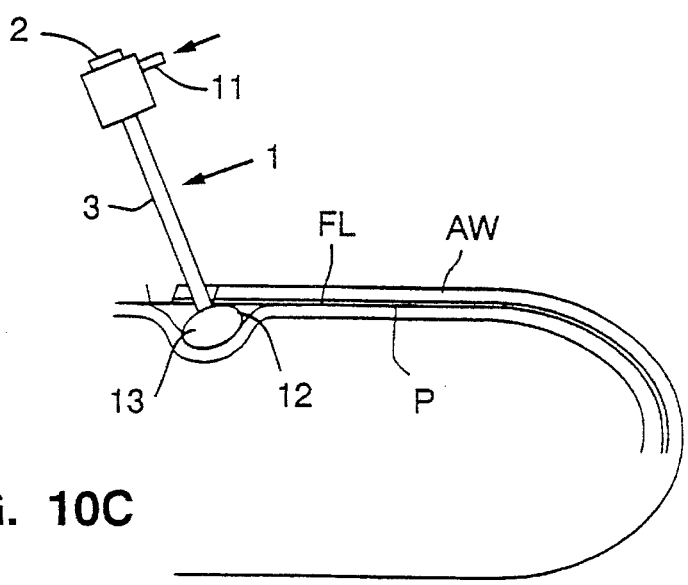

A source of a suitable inflation fluid (not shown), as previously described, is connected to the valve 11. The flow of inflation fluid is turned on, which ejects the main envelope 12 of the main inflatable chamber 13 from the bore of the introducer tube 3. The inflation fluid progressively expands the main envelope 12, and hence the main inflatable chamber 13 defined by the main envelope, into a partially-expanded state, as shown in FIG. 10C. The main envelope expands between the peritoneum and the properitoneal fat layer FL, and gently and progressively detaches an increasing area of the peritoneum P from the underlying layer near the umbilicus as it expands.

An endoscope (not shown) can be inserted into the main inflatable chamber 13 through the flapper valve 2 and the bore of the introducer tube 3. The endoscope can be used to observe the extent of the separation of the peritoneum, as described above.

Figure 10D:
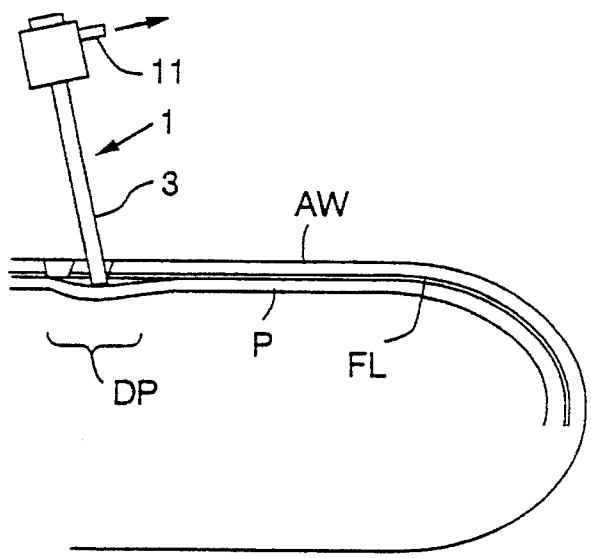

When the main envelope 12 expanded such that the main inflatable chamber 13 is about one-fourth of its fully-expanded diameter, i.e., about 1.0"–1.5" (25–37 mm) in diameter, the supply of inflation fluid is turned off. The valve 11 is then operated to vent inflation fluid from the main inflatable chamber 13. The main envelope progressively returns to its collapsed state, as shown in FIG. 10D. The peritoneum DP that was separated by the main inflatable chamber remains detached from the underlying layer, however, as shown. Alternatively, the main envelope can be inflated to a fully-expanded state.

Figure 10E:
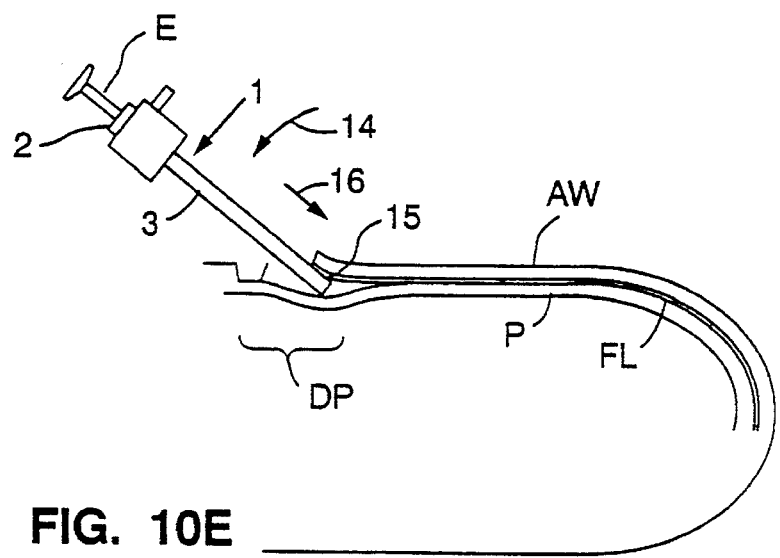

The separation component 1, including the collapsed main envelope 12, is then manipulated in the direction indicated by the arrow 14, and then in the direction indicated by the arrow 16, to advance the distal part 15 of the introducer tube 3 to the limit of the detached part of the peritoneum DP in the direction of the groin, as shown in FIG. 10E. An endoscope E inserted through the flapper valve 2 into the bore of the introducer tube 3 enables the position of the distal part of the introducer tube relative to the detached part of the peritoneum to be observed.

Figure 10F:
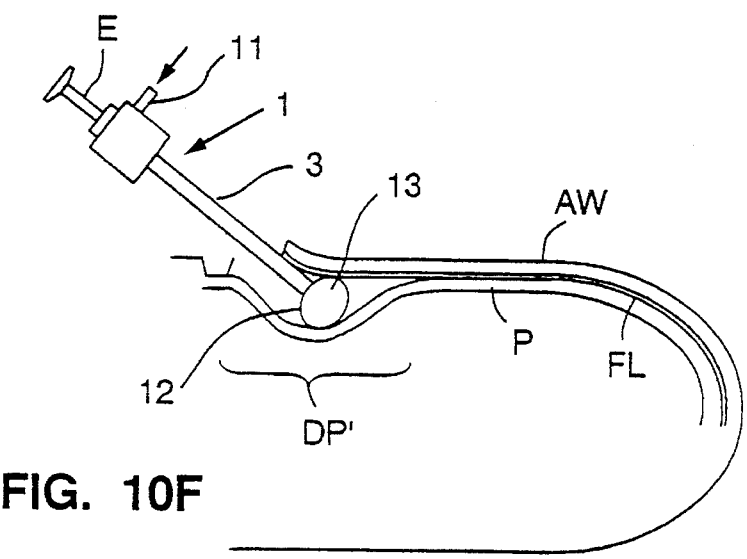

Once the distal part 15 of the introducer tube has been positioned, the separation component 1 is clamped in position, or is gripped, and inflation fluid is once more passed through the valve 11, and the bore of the introducer tube 3 into the main inflatable chamber 13. The main envelope 12 expands once more, increasing the extent of the detached part of the peritoneum towards the groin, as shown in FIG. 10F. The increased extent of the detached part of the peritoneum is indicated by the line DF in the figure. It should be noted that the extent of the detached part of the peritoneum is increased in the direction from the umbilicus to the groin, but not in the direction transverse to this direction. The endoscope E is used to observe the extent of the separation.

The process of collapsing the main envelope 12, advancing the distal part 15 of the introducer tube to the limit of the detached part of the peritoneum DP, in the direction of the groin, holding the introducer tube in position, and partially re-inflating the main envelope 12, is repeated until the detached part of the peritoneum includes the peritoneum over the site of the hernia. This process provides the tunnel T between the incision at the umbilicus and the site of the hernia. This can be seen in FIG. 10I. Alternatively, the main envelope can be fully re-inflated.

Figure 10G:
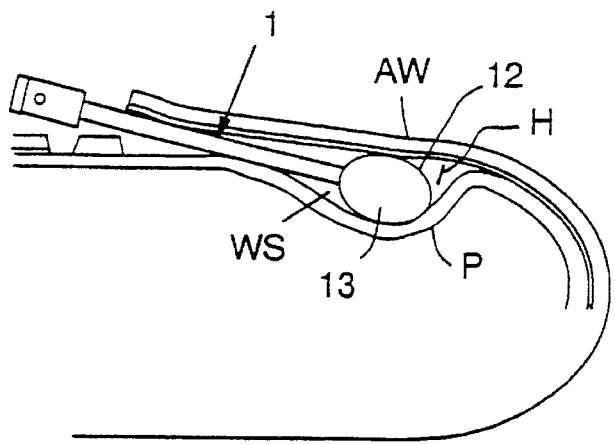

When the main envelope is in the vicinity of the site of the hernia H, the main envelope 12 is fully inflated to form a working space WS including the site of the hernia. This is shown in FIG. 10G.

Figure 10H:
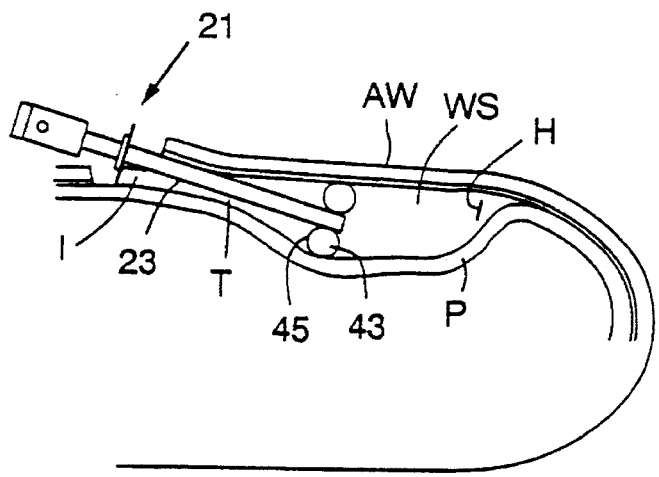

The working space at the site of the hernia is then insufflated. With the two-component apparatus, inflation fluid is vented from the main inflatable chamber 13 to collapse the main envelope 12, and the separation component 1 is withdrawn from the tunnel T through the incision I. The insufflation component 21 is introduced into the incision, and advanced through the tunnel until the envelope 45 of the toroidal inflatable chamber 43 lies within the working space WS, dear of the tunnel. The toroidal inflatable chamber is inflated, the anchor flange is clamped in position, and insufflation gas is passed into the working space, as shown in FIG. 10H. The toroidal inflatable chamber provides a gas-tight seal with the entrance of the tunnel.

Figure 10I:
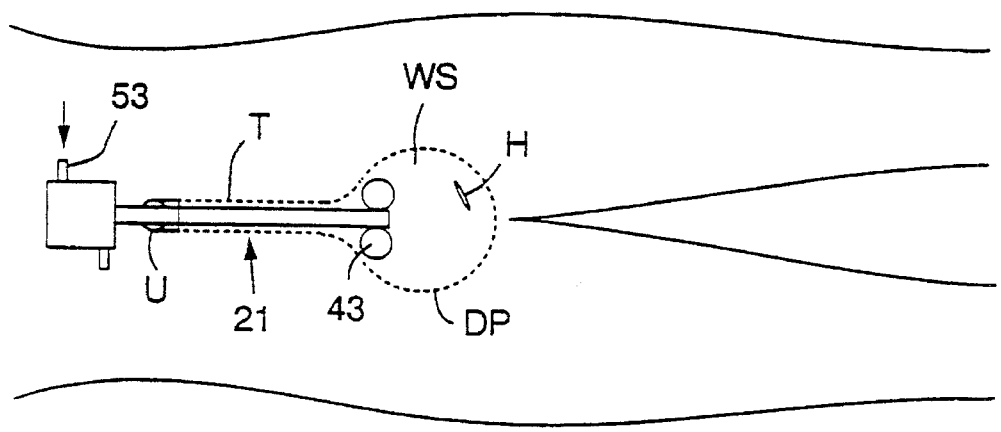

FIG. 10I shows a plan view of the abdomen with the insufflator component 21 in place. The anchor flange has been omitted for clarity. The toroidal inflatable chamber 43 provides a gas-tight seal with the entrance of the tunnel T. The extent of the separated peritoneum is indicated by the dotted line DP. It can be seen that the lateral extent of the separated peritoneum is considerably greater in the working space WS than in the tunnel T.

With the first embodiment of the one-component apparatus, inflation fluid is vented from the main inflatable chamber to collapse the main envelope, and the main envelope is withdrawn from the working space through the bore of the tube assembly. The tube assembly is partially withdrawn until the envelope of the toroidal inflatable chamber lies within the working space, clear of the entrance to the tunnel. The toroidal inflatable chamber is inflated, the anchor flange is clamped in position and insufflation gas is passed into the working space, as already described. The toroidal inflatable chamber seals against the entrance from the tunnel into the working space.

Using the second embodiment of the one-component apparatus, the main envelope is preferably returned to a partially collapsed state, the tube assembly is partially withdrawn until the main inflatable chamber lies within the working space, adjacent to the entrance of the tunnel. The anchor flange is clamped in position, and insufflation gas is passed into the working space, as already described. The partially-collapsed main chamber seals against the entrance from the tunnel into the working space.

If the main envelope is inflated to a fully expanded state during the separation part of the procedure, the whole of the space is insufflated with a gas-tight seal at the incision, as previously described.

Irrespective of the embodiment of the apparatus used to create the insufflated working space WS, the hernia is then repaired using the procedure described in connection with FIG. 3I.

We claim:

1. Apparatus for separating a first layer of tissue from a second layer of tissue and for maintaining separation of the first layer of tissue from the second layer of tissue while providing access to at least one of the layers of tissue, the apparatus comprising:

(a) a main envelope, the main envelope defining a main inflatable chamber;

(b) introducing means for:
  (1) introducing the main envelope in a collapsed state between the first layer of tissue and the second layer of tissue,
  (2) inflating the main envelope into an expanded state to separate the first layer of tissue from the second layer of tissue, and to create a working space therebetween, and
  (3) returning the main envelope to a collapsed state after the working space has been created, the introducing means comprising a single cannula, the single cannula including a main cannula portion whereto the main envelope is attached, and additionally including a bore having a distal end, the bore including a circumferential groove at the distal end;

(c) engaging means for detachably engaging the main envelope with the circumferential groove;

(d) disengaging means for disengaging the engaging means from the circumferential groove and for withdrawing the main envelope from the working space through the bore of the single cannula after the main envelope has been returned to its collapsed state; and (e) insufflating means for introducing insufflation gas into the working space to maintain the separation of the first layer of tissue from the second layer of tissue, the insufflating means including an auxiliary envelope attached to a second portion of the single cannula, the auxiliary envelope defining an auxiliary inflatable chamber.

2. The apparatus of claim 1, wherein the main envelope includes a rolled neck, the rolled neck providing the engaging means.

3. The apparatus of claim 2, wherein the disengaging means comprises a tether attached to the rolled neck.

4. The apparatus apparatus of claim 1, wherein the main envelope includes a neck, and the engaging means comprises an O-ring attached to the neck.

5. The apparatus of claim 4, wherein the disengaging means comprises a tether attached to the O-ring.

6. The apparatus of claim 1, wherein the single cannula provides access for an instrument:

to the main inflatable chamber when the main envelope is in its expanded state, and to the working space after the main envelope has been withdrawn from the working space.

7. Apparatus for separating a first layer of tissue from a second layer of tissue and for maintaining separation of the first layer of tissue from the second layer of tissue while providing access to at least one of the layers of tissue, the apparatus comprising:

(a) a main envelope, the main envelope being elongate and defining a main inflatable chamber;

(b) introducing means for:
  (1) introducing the main envelope in a collapsed state between the first layer of tissue and the second layer of tissues.
  (2) inflating the main envelope into an expanded state to separate the first layer of tissue from the second layer of tissue, and to create a working space therebetween, and
  (3) returning the main envelope to a collapsed state after the working space has been created, the introducing means comprising a single cannula including a bore wherein the main envelope, in the collapsed state, is housed, the main envelope being configured to be withdrawn from the bore of the single cannula by pulling after the main envelope has been returned to its collapsed state; and (c) insufflating means for introducing insufflation gas into the working space to maintain the separation of the first layer of tissue from the second layer of tissue the insufflating means including an auxiliary envelope attached to the single cannula, the auxiliary envelope defining an auxiliary inflatable chamber.

8. The apparatus of claim 7, wherein the single cannula provides access for an instrument:

to the main inflatable chamber when the main envelope is in an expanded state, and to the working space after the main envelope has been withdrawn from the bore of the single cannula.

9. Apparatus for separating a first layer of tissue from a second layer of tissue and for maintaining separation of the first layer of tissue from the second layer of tissue while providing access to at least one of the layers of tissue, the apparatus comprising:

(a) a main envelope, the main envelope defining a main inflatable chamber;

(b) introducing means, for:
  (1) introducing the main envelope in a collapsed state between the first layer of tissue and the second layer of tissue, and
  (2) inflating the main envelope into an expanded state to separate the first layer of tissue from the second layer of tissue, and to create a working space therebetween, the introducing means comprising a single cannula, the single cannula including a main cannula portion whereto the main envelope is attached, the single cannula providing access for an instrument to the main inflatable chamber when the main envelope is in an expanded state;

(c) insufflating means for introducing insufflation gas into the working space to maintain the separation of the first layer of tissue from the second layer of tissue, the insufflating means including an auxiliary envelope attached to an auxiliary cannula portion of the single cannula, the auxiliary_ envelope defining an auxiliary inflatable chamber.

10. The system of claim 9, wherein:

the single cannula includes a bore, the bore including the main cannula portion; and the main envelope is releasably attached to the main cannula portion.

11. The system of claim 9, wherein:

the single cannula includes a bore; and the apparatus additionally comprises access means for providing access to the working space via the bore of the single cannula.

12. The system of claim 11, wherein:

the bore includes the main cannula portion whereto the main envelope is releasably attached; and the access means includes means for removing the main envelope from the bore after the working space has been created and the main inflatable chamber has been returned to the collapsed state.

13. The apparatus of claim 9, wherein:

the single cannula includes a bore, the bore including the main cannula portion; and the main envelope includes a rolled neck, the rolled neck releasably attaching the main envelope to the main cannula portion.

14. The apparatus of claim 13, additionally comprising disengaging means, attached to the rolled neck, for releasing the main envelope from the main cannula portion.

15. The system apparatus of claim 9, wherein the single cannula includes a bore, the bore including the main cannula portion;

the main envelope includes a neck; and the apparatus additionally comprises an O-ring releasably attaching the neck of the envelope to the main cannula portion.

16. The apparatus of claim 15, additionally comprising disengaging means, attached to the O-ring, for releasing the main envelope from the main cannula portion.

17. Apparatus for separating a first layer of tissue from a second layer of tissue and for maintaining separation of the first layer of tissue from the second layer of tissue while providing access to at least one of the layers of tissue, the apparatus comprising:

(a) a main envelope, the main envelope defining a main inflatable chamber;

(b) introducing means for:
  (1) introducing the main envelope in a collapsed state between the first layer of tissue and the second layer of tissue, and
  (2) inflating the main envelope into an expanded state to separate the first layer of tissue from the second layer of tissue, and to create a working space therebetween, the introducing means comprising a single cannula, the single cannula including a main cannula portion whereto the main envelope is attached, and an auxiliary cannula portion having an outer surface and a distal end; and (c) insufflating means for introducing insufflation gas into the working space to maintain the separation of the first layer of tissue from the second layer of tissue, the insufflating means including:

an auxiliary envelope attached to the outer surface of the auxiliary cannula portion adjacent the distal end, the auxiliary envelope defining a generally toroidal auxiliary inflatable chamber, means for inflating the auxiliary inflatable chamber to an expanded state, and flange means, slidably mounted on the auxiliary cannula portion and operating together with the expanded auxiliary inflatable chamber to compress the second layer of tissue, for providing a gas-tight seal.

18. The apparatus of claim 17, wherein the single cannula comprises a first tube mounted coaxially without a second tube to form a lumen therebetween, the first tube including the main cannula portion; and the means for inflating the toroidal inflatable chamber includes the lumen between the first tube and the second tube.

19. The apparatus of claim 17, wherein:

the introducing means is additionally for returning the main envelope to a collapsed state;

the single cannula includes a bore;

the main envelope is elongate and, in the collapsed state, is housed within the bore of the single cannula; and the main envelope is pulled to withdraw the main envelope from the bore of the single cannula after the main envelope has been returned to a collapsed state.

20. The apparatus of claim 17, wherein the auxiliary inflatable chamber comprises an elastomeric material.

21. The apparatus of claim 17, wherein:

the introducing means is additionally for returning the main envelope to a collapsed state;

the single cannula includes a bore having a distal end, the bore including a circumferential groove at the distal end;

the apparatus additionally includes:

engaging means for engaging the main envelope with the circumferential groove, and disengaging means for disengaging the engaging means from the circumferential groove and for withdrawing the main envelope from the working space through the bore of the single cannula after the main envelope has been returned to a collapsed state.

22. The apparatus of claim 21, wherein the main envelope includes a rolled neck, and the rolled neck provides the engaging means.

23. The apparatus of claim 22, wherein the disengaging means comprises a thread attached to the rolled neck.

24. The apparatus of claim 21, wherein:

the main envelope includes a neck, and the engaging means comprises an O-ring attached to the neck.

25. The apparatus of claim 24, wherein the disengaging means comprises a thread attached to the O-ring.

26. The apparatus of claim 21, wherein the single cannula provides access for an instrument:

to the main inflatable chamber when the main envelope is in an expanded state, and to the working space after the main envelope has been withdrawn from the working space.

27. The apparatus of claim 17, wherein the single cannula provides access for an instrument to the main inflatable chamber when the main envelope is in an expanded state.

28. Apparatus for separating a first layer of tissue from a second layer of tissue and for maintaining separation of the first layer of tissue from the second layer of tissue while providing access to at least one of the layers of tissue, the apparatus comprising:

(a) an envelope formed of an elastomeric material, the envelope being substantially cylindrical and having a bore, a first end, and a second end, the envelope being formed with the first end drawn back towards the second end, the envelope defining an inflatable chamber;

(b) introducing means for:

(1) introducing the envelope in a collapsed state between the first layer of tissue and the second layer of tissue, and (2) inflating the envelope into an expanded state to separate the first layer of tissue from the second layer of tissue, and to create a working space therebetween, the introducing means comprising a main cannula portion having a bore, a distal end and a proximal end, the main cannula portion having the first end of the envelope attached to the distal end thereof;

(c) insufflating means for introducing insufflation gas into the working space to maintain the separation of the first layer of tissue from the second layer of tissue, the insufflating means including an auxiliary cannula portion having a bore, a distal end, and a proximal end, the auxiliary cannula portion being mounted within the main cannula portion with the proximal end of the auxiliary cannula portion flexibly coupled to the proximal end of the main cannula portion, the auxiliary cannula portion having the second end of the envelope attached to the distal end thereof; and flange means, slidably mounted on the main cannula portion and operating together with the inflatable chamber to compress the second layer of tissue, for providing a gas-tight seal.

29. The system of claim 28, wherein:

the main cannula portion provides access for an instrument to the inflatable chamber, and the auxiliary cannula portion provides access for an instrument to the working space, the instrument passing through the bore of the main envelope.

30. Apparatus for separating a first layer of tissue from a second layer of tissue and for maintaining separation of the first layer of tissue from the second layer of tissue while providing access to at least one of the layers of tissue, the apparatus comprising:

(a) a main envelope, the main envelope defining a main inflatable chamber;

(b) an auxiliary envelope, the auxiliary envelope defining an auxiliary inflatable chamber;

(c) cannula means for:

(1) introducing the main envelope in a collapsed state between the first layer of tissue and the second layer of tissue, (2) inflating the main envelope into an expanded state to separate the first layer of tissue from the second layer of tissue, and to create a working space therebetween, and (3) introducing insufflation gas into the working space to maintain the separation of the first layer of tissue from the second layer of tissue, the cannula means comprising a bore including a main cannula portion whereto the main envelope is releasably attached, the cannula means additionally comprising an auxiliary cannula portion whereto the auxiliary envelope is attached; and access means for providing access to the working space via the bore of the cannula means, the access means including means for removing the main envelope from the bore of the cannula means after the working space has been created and the main inflatable chamber has been returned to the collapsed state.

31. The apparatus of claim 30, wherein the cannula means is additionally for providing access for an instrument to the main inflatable chamber.

32. Apparatus for separating a first layer of tissue from a second layer of tissue and for maintaining separation of the first layer of tissue from the second layer of tissue while providing access to at least one of the layers of tissue, the apparatus comprising:

a main cannula having a bore, a distal end and a proximal end;

an auxiliary cannula having a bore, a distal end, and a proximal end, the auxiliary cannula being mounted in the bore of the main cannula with the proximal end of the auxiliary cannula portion flexibly coupled to the proximal end of the main cannula, the auxiliary cannula and the main cannula providing a lumen therebetween;

inflatable chamber means for:

separating the first layer of tissue from the second layer of tissue to create the working space therebetween upon inflation from a collapsed state to an expanded state, and providing a gas-tight seal by compressing the second layer of tissue in cooperation with a clamp means slidably mounted on the main cannula, the inflatable chamber means being bounded by an envelope of an elastomeric material, the envelope having a bore, a first end, and a second end, the envelope being formed with the first end drawn back towards the second end, the first end being attached to the distal end of the main cannula, the second end being attached to the distal end of the auxiliary cannula; and means for passing insufflation gas into the bore of the auxiliary cannula for delivery to the working space via the bore of the envelope to maintain the separation of the first layer of tissue from the second layer of tissue.

33. The apparatus of claim 32, wherein:

the main cannula provides access for an instrument to the main inflatable chamber, and the means for passing insufflation gas is additionally for providing access for an instrument to the working space, the instrument passing through the bore of the main envelope.

34. The apparatus of claim 33, wherein the inflatable chamber means is inflated to a fully-expanded state to separate the first layer of tissue from the second layer of tissue, and is inflated to a partially-expanded state to provide the gas-tight seal.

* * * * *